(12) United States Patent
Sy et al.

(10) Patent No.: US 9,492,472 B2
(45) Date of Patent: Nov. 15, 2016

(54) COMPOSITIONS AND METHODS OF TREATING CANCER

(75) Inventors: Man Sun Sy, Shaker Heights, OH (US); Wei Xin, Solon, OH (US); Chaoyang Li, Mayfield Heights, OH (US); Shuiliang Yu, Cleveland, OH (US); Shaoman Yin, Atlanta, GA (US)

(73) Assignee: Case Western Reserve University, Cleveland, OH (US)

( * ) Notice: Subject to any disclaimer, the term of this patent is extended or adjusted under 35 U.S.C. 154(b) by 1031 days.

(21) Appl. No.: 13/141,437

(22) PCT Filed: Dec. 23, 2009

(86) PCT No.: PCT/US2009/069425
§ 371 (c)(1),
(2), (4) Date: Jun. 22, 2011

(87) PCT Pub. No.: WO2010/075521
PCT Pub. Date: Jul. 1, 2010

(65) Prior Publication Data
US 2011/0257102 A1 Oct. 20, 2011

(51) Int. Cl.
*A61K 39/00* (2006.01)
*A61K 31/7088* (2006.01)
*A61K 31/00* (2006.01)
*A61K 38/17* (2006.01)

(52) U.S. Cl.
CPC .......... *A61K 31/7088* (2013.01); *A61K 31/00* (2013.01); *A61K 38/177* (2013.01)

(58) Field of Classification Search
None
See application file for complete search history.

(56) References Cited

U.S. PATENT DOCUMENTS 5,773,572 A * 6/1998 Fishleigh et al. ............ 530/324
8,158,373 B2 4/2012 Sy
2003/0219459 A1 11/2003 Bachmann et al.
2005/0260639 A1 11/2005 Nakamura et al.
2009/0252721 A1 10/2009 Buschmann et al.

FOREIGN PATENT DOCUMENTS

WO  WO 01/97785 A2  12/2001
WO  WO 2005/026735 A2  3/2005

OTHER PUBLICATIONS

Rudinger. In Peptide Hormones, J. A. Parsons, ed. University Park Press, Baltimore, 1976, pp. 1-8.*
Ashok, Aarthi et al., "Retrotranslocation of Prion Proteins from the Endoplasmic Reticulum by Preventing GPI Signal Transamidation", Molecular Biology of the Cell, vol. 19, 3463-3476, Aug. 2008.
Chen, Rui, et al., "Comparative Efficiencies of C-Terminal Signals of Native Glycophosphatidylinositol (GPI)—Anchored Proproteins in Conferring GPI—Anchoring", Journal of Cellular Biochemistry 84:68-83 (2001).
Kim, SJ, et al., "Over-Expression of Cellular Prion Protein is Unique in Pancreatic Endocrine Tumors", Modern Pathology, Feb. 2007 20 Suppl 2:102A.
Tockman, Melvyn S., et al., "Consideration in Bringing a Cancer Biomarker to Clinical Application", Cancer Research (Suppl.), 2711s-2718s, May 1, 1992.
Wanek, Gerald L, et al., "Conversation of a PI-Anchored Protein to an Integral Membrane Protein by a Single Amino Acid Mutation", Nature, 1988, 242:697-699.
Greenwood, et al., Cell Line Dependent RNA Expression Profiles of Prion-infected Mouse Neuronal Cell, J. Mol Biol (2005) vol. 349, No. 3, p. 487-500.
GenBank: AAG21693.1, "Prion protein [Homo sapiens]" Nov. 3, 2000, [retrieved on Apr. 6, 2010] Retrieved from the National Center for Biotechnology Information protein database the using the internet: <URL: http:www.ncbi.nlm.nih.gov/protein/AAG21693.1>.

* cited by examiner

Primary Examiner — Sean Aeder
(74) Attorney, Agent, or Firm — Tarolli, Sundheim, Covell & Tummino LLP

(57) ABSTRACT

A method of inhibiting neoplastic, cancer, and/or tumorgenic cell proliferation, cell growth and motility in a subject includes administering to a cancer cell expressing Pro-PrP and FLNa a therapeutically effective amount of a Pro-PrP regulating agent.

13 Claims, 24 Drawing Sheets

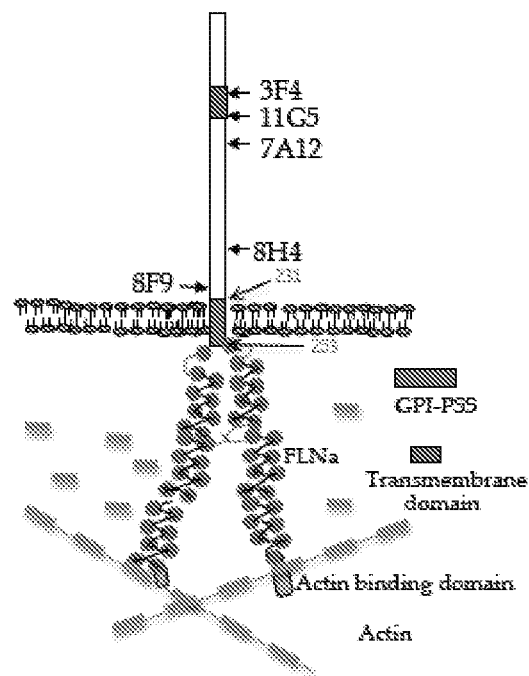
Fig. 6
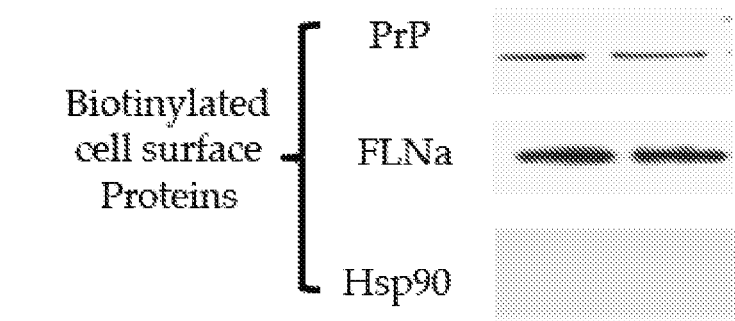
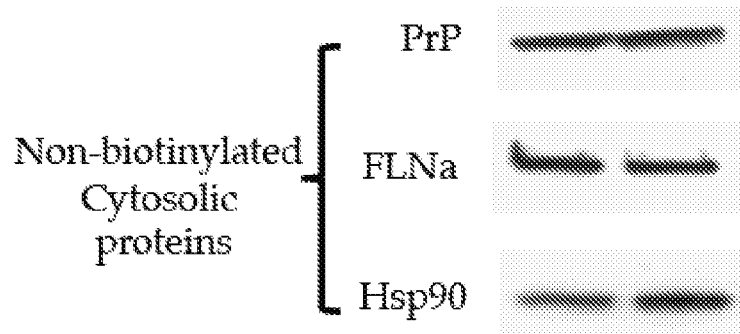
Fig. 7

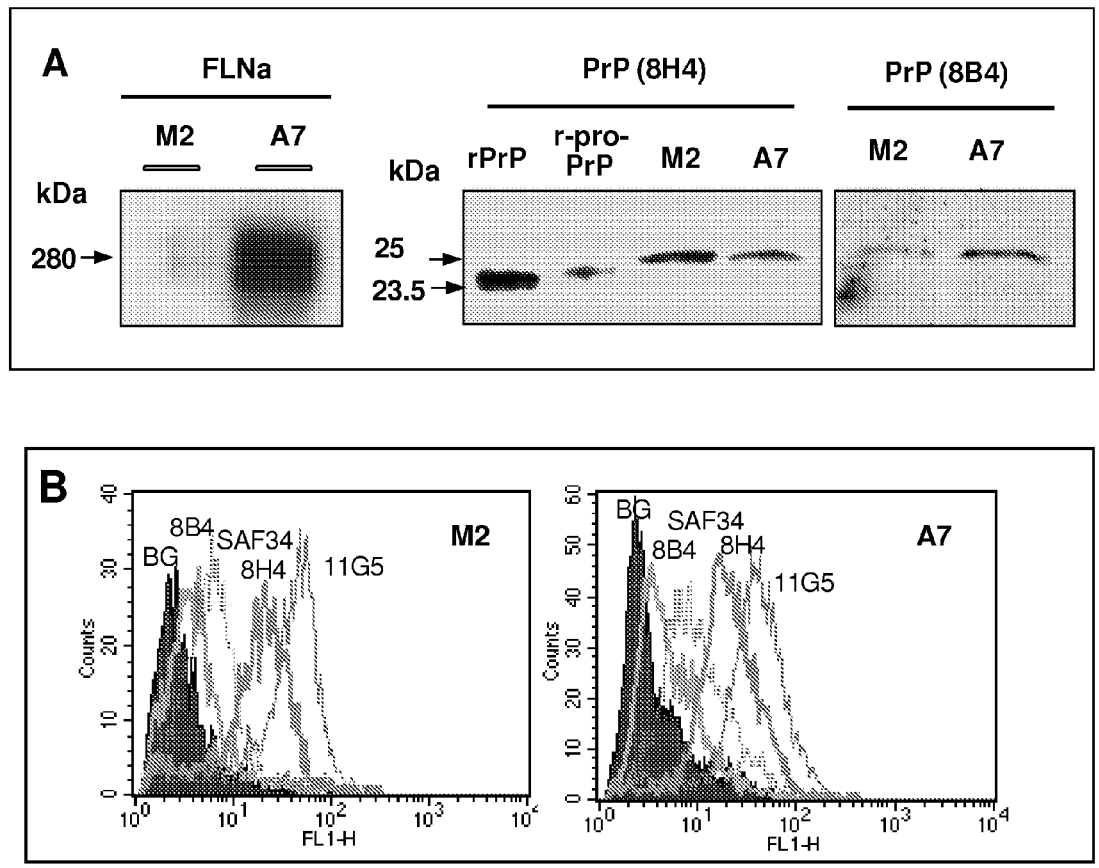
Figs. 13A-B

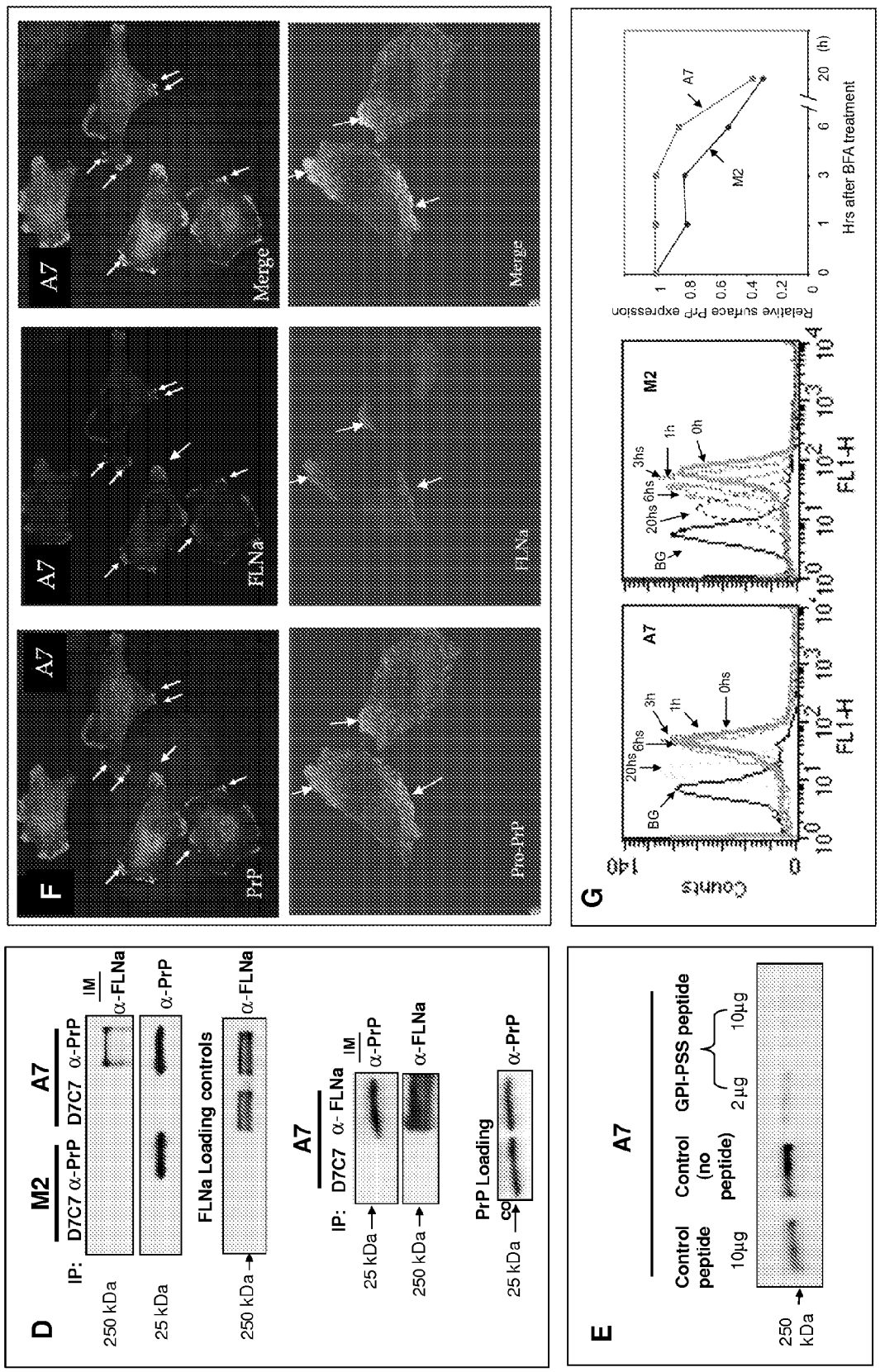
Figs. 13D-G

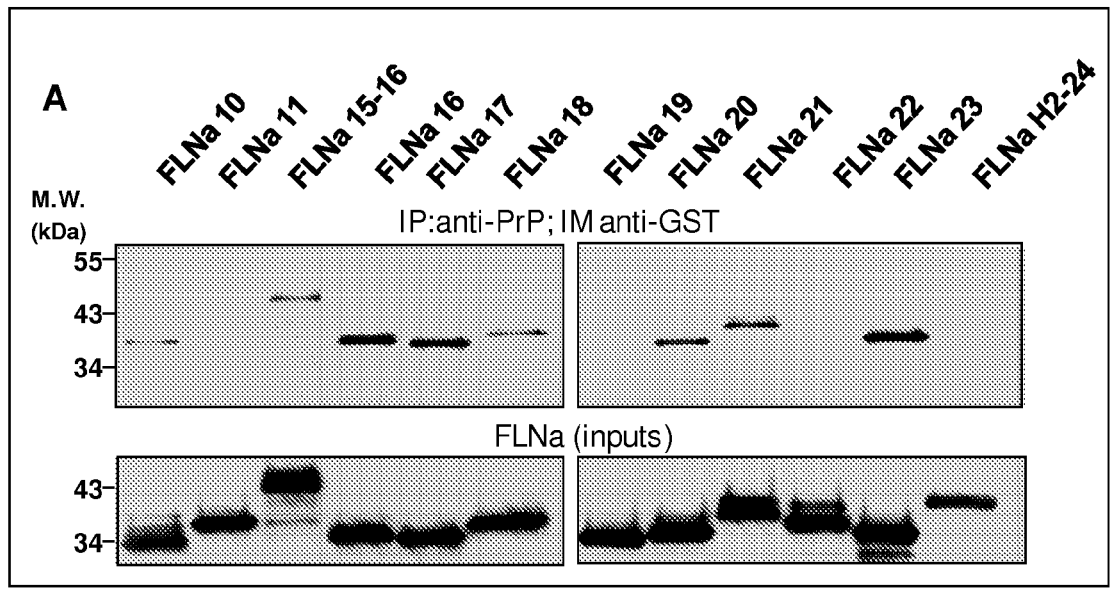
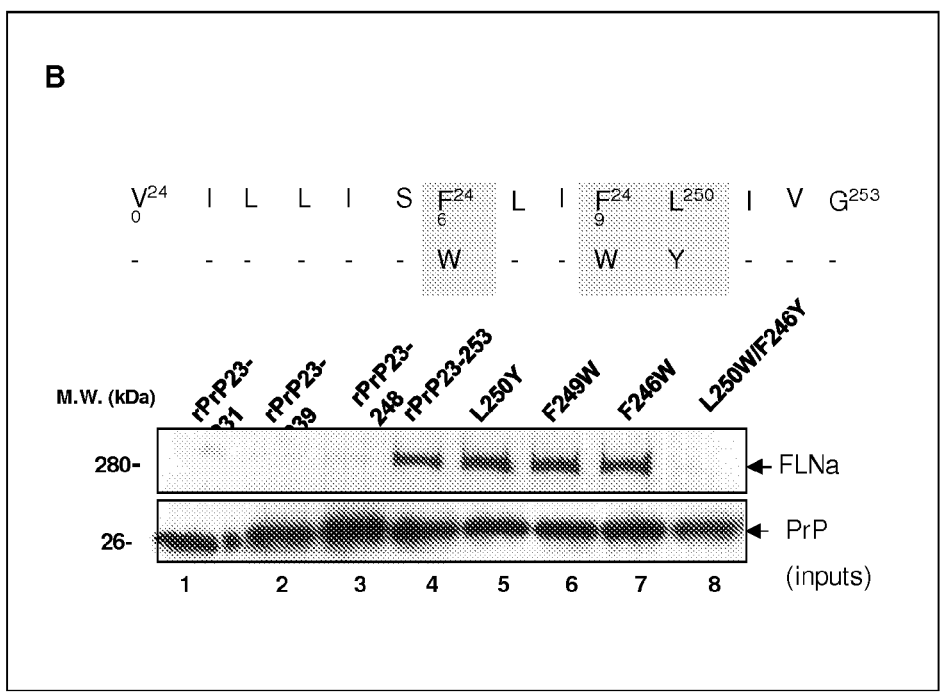
Figs. 14A-B

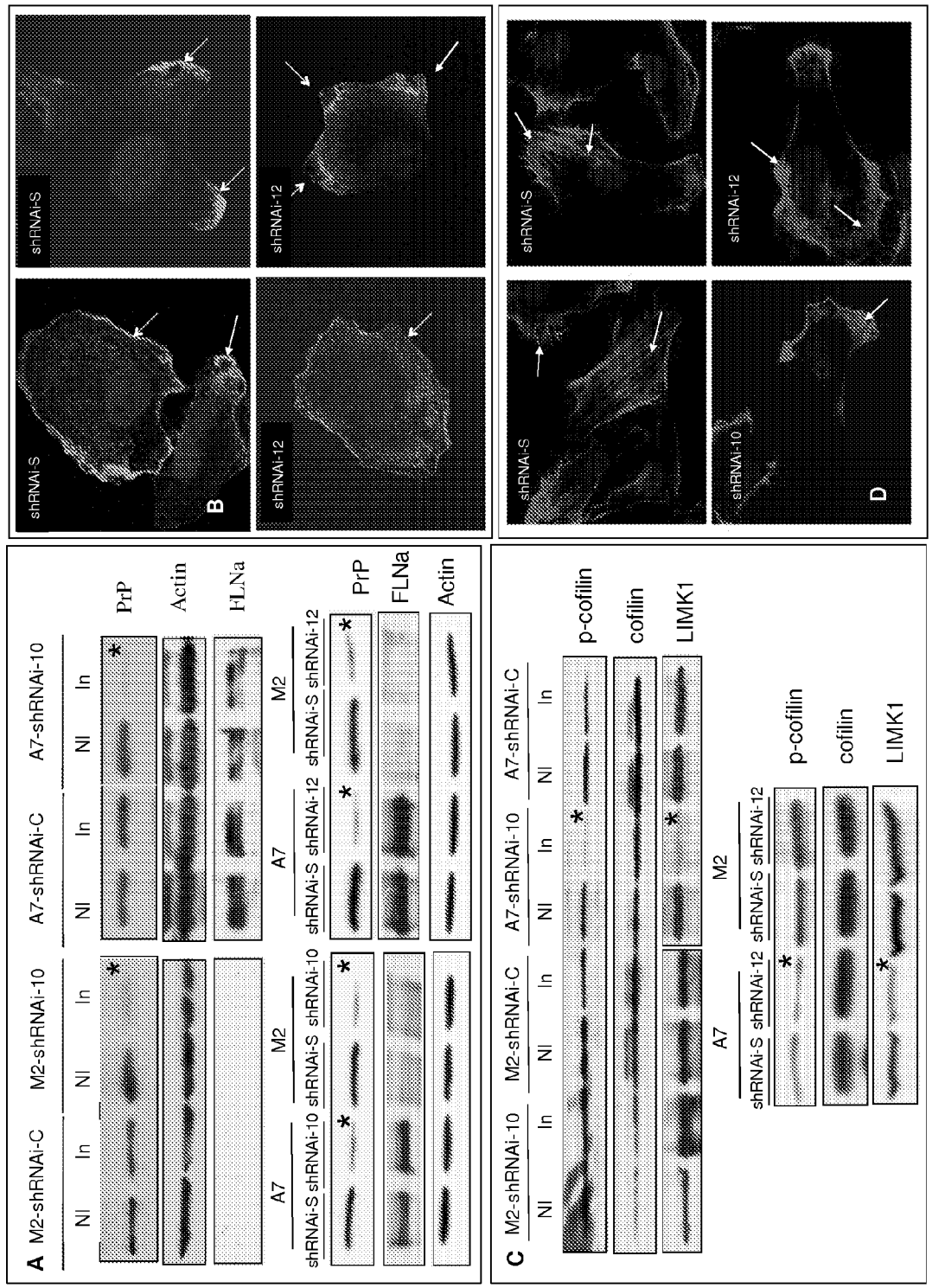
Fig. 15A-D

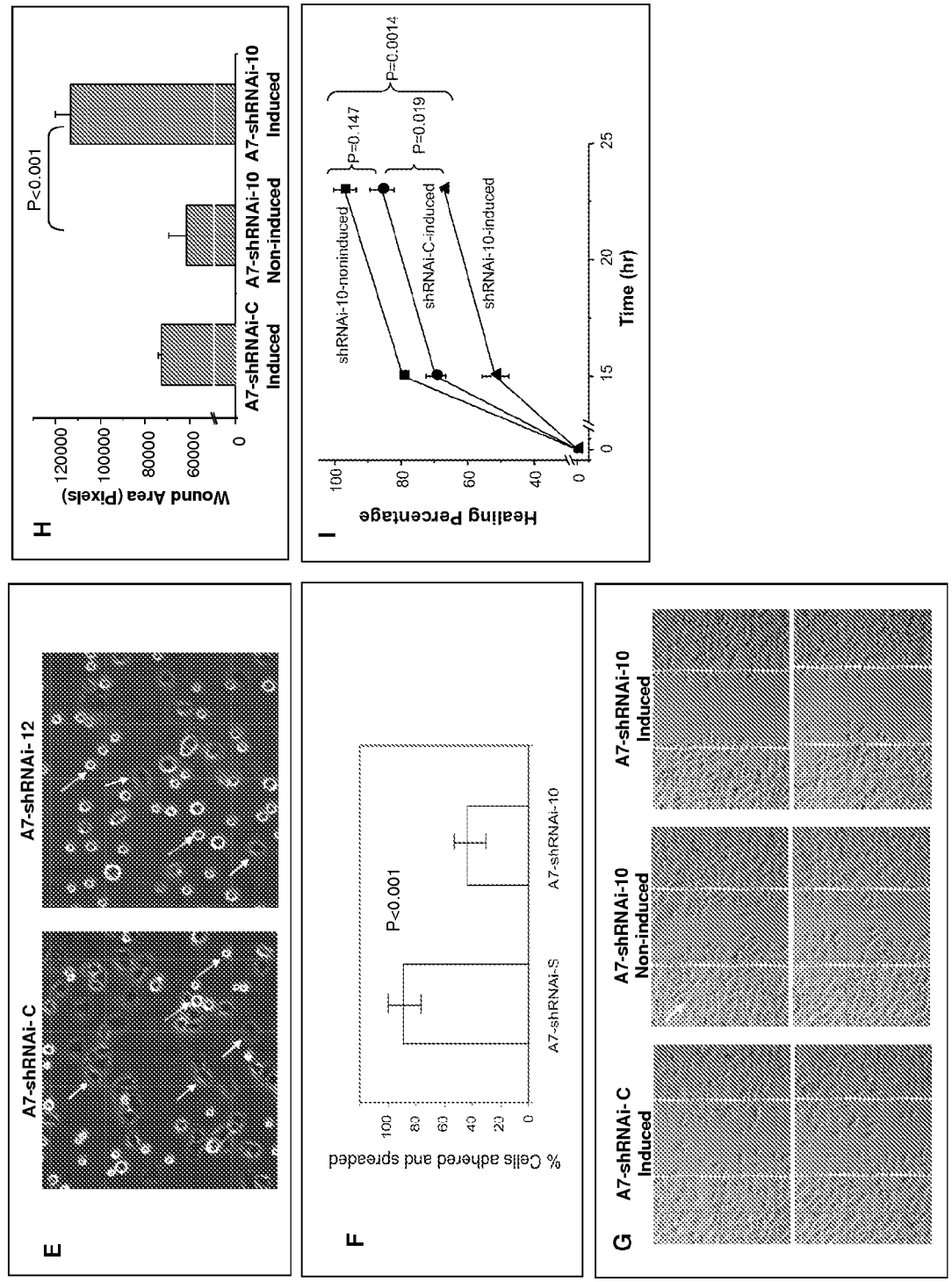
Figs. 15E-I

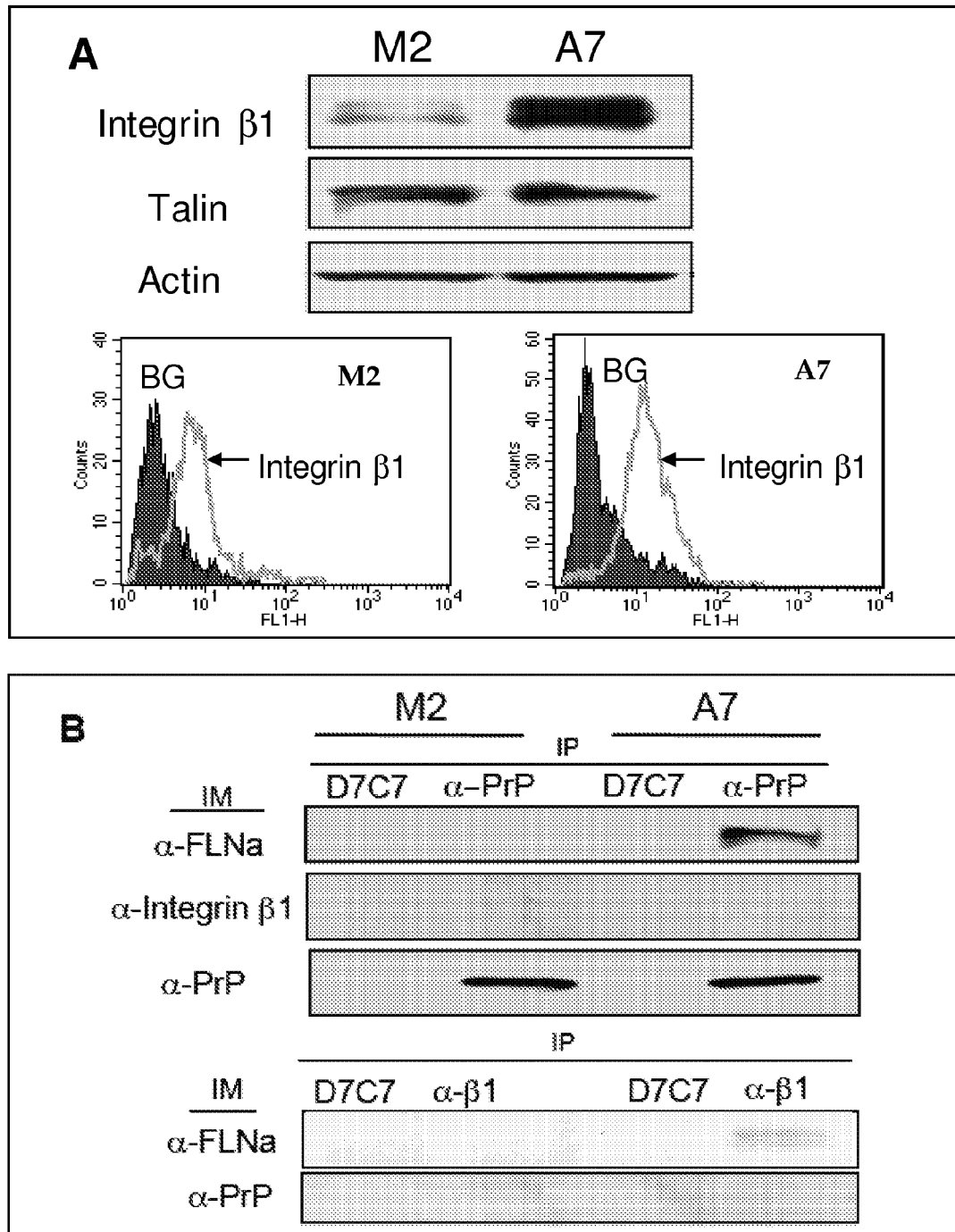
Figs. 16A-B

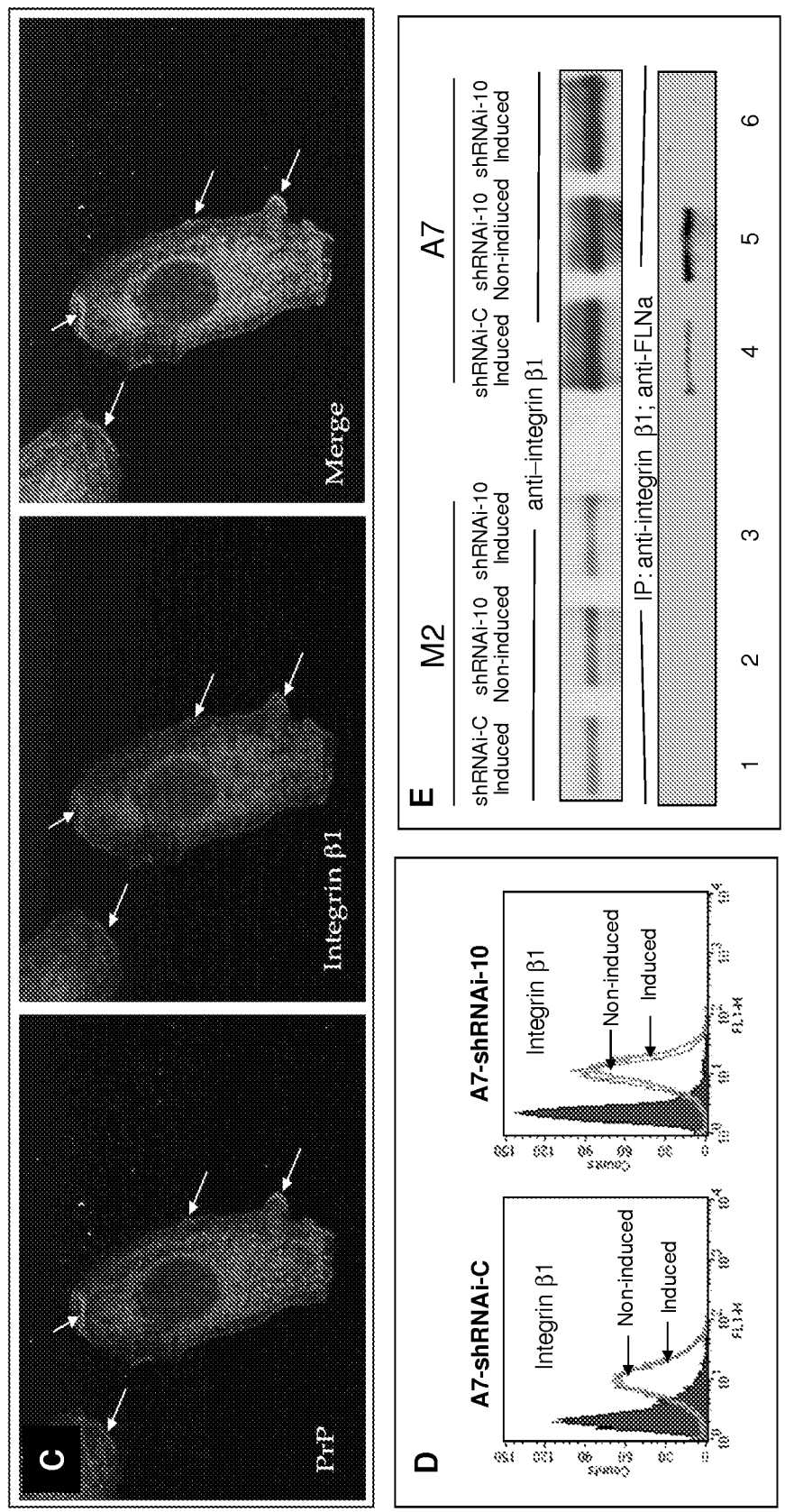
Figs. 16C-E

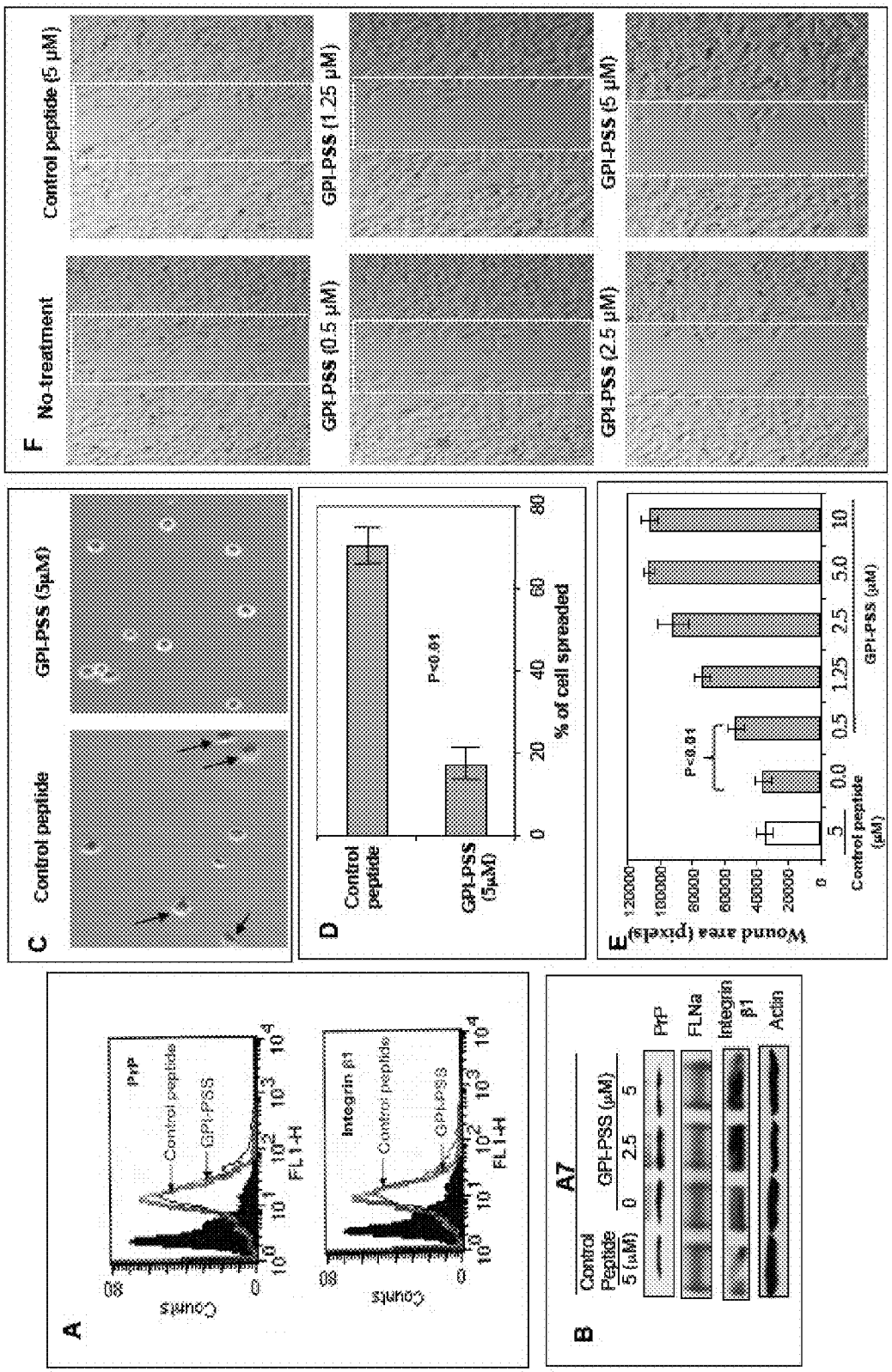
Figs. 18A-F

COMPOSITIONS AND METHODS OF TREATING CANCER

RELATED APPLICATION

This application corresponds to PCT/US2009/069425, filed Dec. 23, 2009, which claims the benefit of U.S. Provisional Application No. 61/140,130, filed Dec. 23, 2008, the subject matter of which is incorporated herein by reference in their entirety.

FIELD OF THE INVENTION

The present invention relates to compositions and methods of treating cancer and, particularly, relates to compositions and methods of treating cancer, tumorgenic, and/or neoplastic cells expressing prion protein.

BACKGROUND

Normal cellular prion protein (PrP) is a highly conserved, widely expressed, glycophospholinositol (GPI)-anchored cell surface glycoprotein. Since its discovery, most studies on PrP have focused on its role in a group of neurodegenerative conditions, known as prion diseases. Little is known about PrP outside the nervous system.

The synthesis, processing and transit of PrP to the cell surface are complex and not completely understood. Normally, PrP is present in lipid rafts and can function as a signaling molecule.

PrP has many binding partners, such as glycosyaminoglycans, copper, laminin receptor, N-CAM, heat shock proteins, dystroglycan, stress-inducible protein, selectin and glypican-1. PrP also binds Grb2, an adapter protein, lipids and nucleic acids. PrP plays a role in apoptosis in a cell context dependent manner.

Prions prevent neuronal cell-line death. A recent study found that normal PrP is involved in the proliferation of epithelial cells and in the distribution of junction associated proteins in human enterocytes in vitro and in intestine in vivo. On the other hand, since the PrP deficient ($Prnp^{-/-}$) mouse is viable and appears to be normal, the physiologic functions of PrP remain an enigma.

SUMMARY OF THE INVENTION

The present invention relates to a method of inhibiting adhesion, motility, migration, dispersal, and/or metastasis of a neoplastic, cancer, and/or tumorgenic cell in a subject. The cancer cell expresses pro-prion protein (pro-PrP) and filamin A (FLNa). The method includes administering to the cell a therapeutically effective amount of a pro-PrP regulating agent.

In an aspect of the invention, the pro-PrP regulating agent can include a peptide or nucleic acid that inhibits the activity or expression of pro-PrP in a cell. The pro-PrP regulating agent can also include a competitive inhibitor of the FLNa binding domain of pro-PrP and/or the pro-PrP binding domain of FLNa. The competitive inhibitor can include a peptide, which inhibits binding of pro-PrP and FLNa in the cell.

In another aspect of then invention, the pro-PrP regulating agent can include a peptide consisting of about 5 to about 15 amino acids that are substantially homologous to consecutive amino acids of the amino acid sequence of the GPI-PSS domain of pro-PrP. In one example, the peptide can include an amino acid sequence selected from the group consisting of SEQ ID NO: 2, SEQ ID NO: 3, SEQ ID NO: 4, SEQ ID NO: 5, and SEQ ID NO: 6.

The Pro-PrP regulating agent can also include one more of small interfering RNAs, antisense oligonucleotides, neutralizing antibodies, small molecules, recombinant gene expression vectors, recombinant gene viral vectors, synthetic peptides, recombinant polypeptides, peptidomimetics and inhibitors of the regulatory regions of PRNP.

The cancer cells treated by the pro-PrP regulating agent can include, for example, at least one of pancreatic adenocarcinoma cancer cell lines (PDAC), hepatocarcinoma cell lines, melanoma cell lines, colon carcinoma cell lines, gastric cancer cell lines, or colorectal cancer cell lines.

The present invention also relates to a pharmaceutical composition for inhibiting adhesion, motility, migration, dispersal, and/or metastasis of a cancer cell expressing pro-PrP and FLNa. The pharmaceutical composition includes a peptide consisting of about 5 to about 15 amino acids that are substantially homologous to consecutive amino acids of the amino acid sequence of the GPI-PSS domain of pro-PrP. In one aspect of the invention, the peptide can have an amino acid sequence selected from the group consisting of SEQ ID NO: 2, SEQ ID NO: 3, SEQ ID NO: 4, SEQ ID NO: 5, and SEQ ID NO: 6. In another aspect of the invention, the peptide can include a transport moiety to facilitate transport of the peptide within the cancer cell. The transport moiety can include, for example, a peptide having an amino acid sequence of SEQ ID NO: 7.

The present invention further relates to a method of detecting cancer or an increased likelihood of cancer in a subject. The method includes obtaining a bodily sample from the subject and detecting a level of pro-PrP in the sample. The level of pro-PrP in the sample is then correlated to the presence or increased likelihood of cancer in the subject.

In an aspect of the invention, the bodily sample can include blood, plasma, or serum from the subject. The level of pro-PrP can be detected by an immunoassay. In one example, the cancer can include pancreatic cancer and the bodily sample can include supernatant from the pancreatic cancer cells.

BRIEF DESCRIPTION OF THE DRAWINGS

FIG. 6 illustrates a hypothetic model of some of the pro-PrP on the cell surface of PDAC. A portion of the C-terminus of the PrP-GPI-PSS may be exposed facing the cytoplasm, we found that the last 5 amino acids from 249 to 253 of the PrP-GPI-PSS is essential for binding FLNa. The arrows indicate the epitope of the mAbs.

FIG. 7 illustrates an immunoblot showing cell surface PrP co-purifies with FLNa but not Hsp90. Cell surface proteins from the PDAC cell lines were biotinylated and immunoprecipitated with avdin conjugated beads. Bound proteins were then separated by SDS-PAGE and then immunoblotted with mAbs specific for PrP, FLNa or Hsp90. It is clear that the affinity-purified proteins contain PrP and FLNa but not Hsp90. On the other hand, all three proteins are detected in the non-biotinylated cytosolic fraction.

FIG. 15 illustrates the effects of "knocking-down" PrP in M2 and A7 cells (A). Immunoblots show that down regulation of PrP in M2 and A7 cells reduces the levels of PrP in both cell lines, but does not reduce the expression level of FLNa in A7 cells. Top panels show shRNA under the control of an inducible promoter. (NI=non-induced, In=induced). Bottom panels show constitutively active shRNA. (B). Confocal microscopic photos show that down regulation of PrP alters the spatial distribution of FLNa in A2 cells. In PrP down regulated cell, FLNa immunoreactivity in the inner membrane areas is reduced (bottom left panel, see arrow), or FLNa appears to retract from the leading edges (bottom right panel, see arrows). (C). Down regulation of PrP reduces the expression levels of p-cofilin-1 and LIMK-1 in A7 cells but not in M2 cells indicating that the effects on p-cofilin-1 and LIMK-1 expression is FLNa dependent. (D). Down regulation of PrP alters the organization of actin filaments. In control cells with shRNA-S (top two panels), actin filaments are better organized (see arrows). In PrP down regulated A7 cells, the actin filaments are disorganized in certain areas of the cells (bottom panels, arrows identified areas of actin disorganization. (E). Microscopic photos show that PrP down regulated A7 cells are much less adhesive. Solid arrows identify adherent cells, while dashed arrows identify nonadherent floating cells. (F). Quantification of results showing that PrP down regulated A7 cells are less able to adhere and spread. Results presented were the average of the four wells +/−S.E. (standard error). (G). Microscopic photos show that PrP down regulated A7 cells have reduced cellular migration in a wound healing assay. Photos were taken at 15 hrs post wound initiation. Two representative wells from each condition were shown. (H). Quantification of the wound healing assay taken at 15 hrs post wound initiation. PrP down regulated A7 cells have reduced would-healing capacity. Results presented were the average of the triplicate wells +/−S.E. (I). Quantification of wound-healing assay at different time points after wound healing. PrP down regulated A7 cells have reduced would-healing capacity at all time points. Results presented were the average of the triplicate wells +/−S.E.

FIG. 16 illustrates the co-purification of FLNa and integrin β1 and the effects of downregulation of PrP on integrin β1 and FLNa association. (A) Immunoblots show that A7 cells have more integrin β1 than M2 cells, but the levels of talin in the two cell lines are comparable. Histograms show that A7 cells also have more cell surface integrin β1 than M2 cells. (B) Immunoblots show that PrP co-purifies with FLNa, and integrin β1 copurifies with FLNa, but PrP does not co-purify with integrin β1 in A7 cells. (C). Confocal microscopic photos show that integrin β1 and PrP are partially colocalized in A7 cells. (D). Histograms show that down regulation of PrP does not change the expression levels of cell surface integrin β1 on A7 cells. (E) Immunoblots show that down regulation of PrP does not alter the expression levels of integrin β1 (top panel), but reduced the amounts of integrin β1 copurified with FLNa (bottom panel).

FIG. 18 illustrates A PrP-GPI-PSS with cell penetrating capacity inhibits A7 cell spreading and migration. (A). Histograms show that incubation of A7 cells with the KKRPK-PrP-GPI-PSS (SED ID NO: 8) (5 μM) for 15 hrs did not alter the expression levels of either PrP or integrin β1 on the cell surface. (B) Immunoblots show that incubation of A7 cells with the KKRPK-PrP-GPI-PSS (SEQ ID NO: 8) (5 μM) for 15 hrs did not alter the expression of total PrP, FLNa and integrin β1. (C). Quantification of the cell spreading results. Results presented were the average +/−S.E. of the triplicate wells. (D). Photographs of microscopic images show that incubation with a KKRPK-PrP-GPI-PSS (SEQ ID NO: 8) synthetic peptide reduces A7 cell spreading. Arrows identify the adherent cells. (E). Quantification of the wound-healing assay. Results presented were the average +/−S.E. of the triplicates. The KKRPK-PrP-GPI-PSS (SEQ ID NO: 8) inhibited the migration of A7 cells by approximately 50 to 60%. Results presented were the average +/−S.E. of the triplicate wells. (F). Representative photographs of microscopic images show that incubation with a KKRPK-PrP-GPI-PSS (SEQ ID NO: 8) synthetic peptide in A7 cell reduces cellular migration, in a wound-healing assay and in a peptide concentration dependent manner. The images were takes at 15 hrs after the initiation of wound. Areas between two white lines mark the original wound area.

DESCRIPTION

Figure 1:
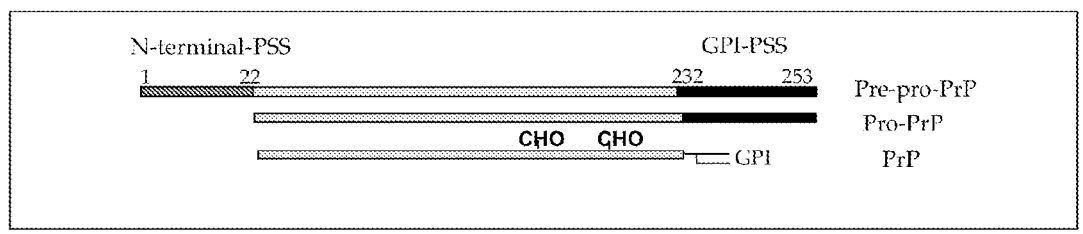
FIG. 1 is a schematic diagram showing the synthesis and processing of PrP. CHO=N-linked glycans.

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, the terms "epithelial cells" or "epithelial tissue" are used in their broadest sense and refer to those cells, which form one or more layers of cells covering an external surface or lining a cavity throughout the body of a mammal.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isosteres). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular, a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the tissue treated, such that it enters the animal's system and, thus, is subject to metabolism and other like processes, for example, subcutaneous administration.

As used herein, the term "GPI anchor" means a glycosylphosphatidylinositol anchor that some proteins use to attach to the outer membrane leaflet of a cell.

As used herein, the term "Pre-Pro-PrP" means a precursor of the mature prion protein that contains the N-terminal peptide signal sequence as well as the C-terminal GPI anchor peptide signal sequence.

As used herein, the term "pro-Prp" means a precursor of the mature prion protein, in which the N-terminal peptide sequence has been removed but retains the C-terminal GPI anchor peptide sequence. This sequence is removed prior to the addition of the GPI anchor.

As used herein, the term "PrP" means a mature prion, which is a highly conserved, widely expressed glycoprotein that is tethered to the outer cell surface by a GPI anchor.

As used herein, the term "PrP$^{sc}$" means a scrapie prion, an abnormal, rogue isoform of the normal PrP that is pathogenic and infectious.

As used herein, the term "Filamin A (FLNa)" means a cytolinker, which links cell surface receptors to actin filaments. FLNa is an integrator of the cell signaling and cell mechanical force.

The present invention relates to compositions and methods of inhibiting neoplastic, tumorgenic, and/or cancer cell adhesion, motility, migration, dispersal, and/or metastasis by administering to a neoplastic, tumorgenic, and/or cancer cell expressing pro-PrP and filamin A (FLNa) a therapeutically effective amount of a pro-PrP regulating agent. The present invention also relates to pharmaceutical compositions for use in the methods of the invention to treat a subject.

Human PrP is first synthesized as a pre-pro-PrP polypeptide of 253 amino acids as is schematically illustrated in FIG. 1. The first 22 amino acids at the N-terminus contain the leader peptide sequence. The last 22 amino acids at the C-terminus contain the GPI anchor peptide sequence (GPPSS). Both of these sequences are removed in the endoplasmic reticulum, and thus in most normal cells are absent from mature PrP. Mature PrP has 209 amino acids from residue 23 to 231 and can arbitrarily be divided into three domains. The N-terminal domain encompasses the first 90 amino acids, and has a conserved motif of five repeating octapeptides. The central domain is located between amino acid 110 and 130. The C-terminal region contains a well-defined globular domain, which has two potential N-linked glycosylation sites and a disulfite bridge. Addition of two N-linked glycans, and GPI anchor completes the maturation of GPI-anchored PrP, which has a molecular mass of about 34-39 kDa.

PrP is expressed in certain human cancers or human cancer cell lines, such as pancreatic ductal adenocarcinoma cancer cell lines (PDAC), hepatocarcinoma cell lines, melanoma cell lines, colon carcinoma cell lines, gastric cancer cell lines, and colorectal cancer cell lines. However, in contrast to normal PrP, which is glycosylated and GPI-anchored, in certain human cancer cell lines PrP is neither glycosylated nor GPI-anchored. Instead, PrP in these cancer cells exists as pro-PrP retaining it GPI anchor peptide signal sequence. Despite lacking a GPI anchor, pro-PrP is present on and/or attached to the cancer cell surface using the GPI-PSS as a transmembrane anchoring domain.

Figure 2:
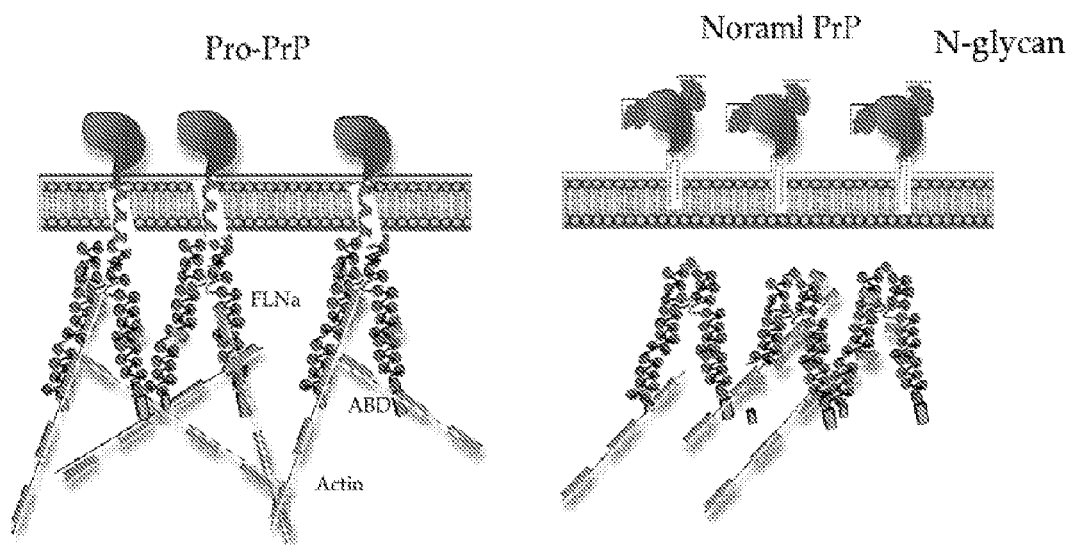
FIG. 2 is a schematic diagram of cell surface pro-PrP and normal, glycosyated, GPI-anchored PrP-Cell surface pro-PrP is using the GPI-PSS as a transmembrane domain. The GPI-PSS transverses the membrane and interacts with FLNa. The actin-binding domain (ABD) of FLNa binds actin filaments. The normal PrP is GPI-anchored, glycosylated and does not interact with FLNa.

As illustrated schematically in FIG. 2, the GPI-PSS of pro-PrP has a filamin A (FLNa) binding motif that is able to transverse the cancer cell membrane bi-layer enabling it to bind to and/or complex with FLNa that is expressed by the cancer cell. FLNa is an actin binding cytolinker, which connects cell surface molecules to the actin filaments of the cytoskeleton and thus integrates signaling events with cellular mechanical forces. FLNa binds actin and promotes actin filament branching to maintain a three dimensional orthogonal network at the leading edges of a moving cell.

The formation of a complex between and/or binding of pro-PrP and FLNa in cancer cells was found to disrupt the normal function of FLNa. For example, it was found that binding of pro-PrP to FLNa disrupts the cytoskeletal organization of cancer cells by perturbing the normal functions of FLNa and contributes to the aggressiveness of certain cancers. It was also found that in certain cancers (e.g., human pancreatic cancers), a subgroup (e.g., 41%) of patients expresses pro-PrP in their tumors, and PrP expression in tumors correlates with markedly decreased survival of the patient.

Inhibiting pro-PrP expression in cancer cells that normally express pro-PrP and FLNa, however, alters the cytoskeleton and cell signaling, and reduces cancer cell proliferation and invasiveness in vitro and growth in vivo. Agents that regulate pro-PrP function (i.e., pro-PrP regulating agents) can therefore be used to inhibit adhesion, motility, migration, dispersal, and/or metastasis of cancer cells that express pro-PrP and FLNa.

An aspect of the invention therefore relates to a method of treating cancers expressing pro-PrP and FLNa in a subject by administering to the cancer an amount of a pro-PrP regulating agent to the subject effective to inhibit the expression or activity of pro-PrP itself and/or the binding of Pro-PrP to its ligands, such as filamin A (FLNa). The methods of the present invention can be used to treat a subject and, in particular, a human.

The "pro-PrP regulating agent" or "agent that regulates pro-PrP" can include any composition or substance (e.g., DNA, RNA, protein, or small molecules) that decreases the gene or expressed gene product, pro-PrP, and/or suppresses the functional activity of pro-PrP-FLNa binding in the cancer cells. Decreasing the expression level of the PrP gene (PRNP) or gene product can be accomplished in a number of ways known to those with skill in the art including, for example: silencing of the PrP; targeted disruption of the positive transcriptional regulatory regions of PrP; inhibition of the gene or gene products of positive transcriptional or translational regulators of the pro-PrP (e.g., using antisense oligonucleotides, small interfering RNAs, neutralizing antibodies, dominant negative genes/polypeptides, peptidomimetics, small molecules); increasing the activity or expression of negative transcriptional or translational regulators of PrP (e.g., using recombinant gene expression vectors, recombinant viral vectors synthetic peptides, recombinant polypeptides, hypermorphic genes/polypeptides) or inhibition of pro-PrP itself (e.g., using antisense oligonucleotides, small interfering RNAs, neutralizing antibodies, dominant negative polypeptides, peptidommetics, small molecules).

The functional activity of pro-PrP can be suppressed, inhibited, and/or blocked by, for example, direct inhibition of the activity of the pro-PrP protein (e.g., by using neutralizing antibodies, small molecules or peptidomimetics, dominant negative polypeptides); inhibition of genes and/or proteins that activate PrP (e.g., by blocking the expression or activity of the genes and/or proteins); activation of genes and/or proteins that inhibit pro-PrP (e.g., by increasing the expression or activity of the genes and/or proteins); inhibition of genes and/or proteins that are downstream mediators of the pro-PrP function (e.g., by blocking the expression and/or activity of the mediator genes and/or proteins); introduction of genes and/or proteins that negatively regulate the pro-PrP (e.g., by using recombinant gene expression vectors, recombinant viral vectors or recombinant polypeptides); or gene replacement with, for instance, a hypomorphic mutant of pro-PrP (e.g., by homologous recombination, over-expression using recombinant gene expression or viral vectors, or mutagenesis).

Since a portion of the pro-PrP protein binds to and/or complexes with FLNa, any compound or composition that interferes with this binding can interfere with the function of pro-PrP in binding FLNa. It is shown in the examples below that a pro-PrP competitive inhibitor peptide is a potent inhibitor of spreading, migration, and/or motility of cancer cells expressing pro-PrP and FLNa as it leads to a decrease in pro-PrP and FLNa binding.

In one embodiment of the present invention, the pro-PrP regulating agent can bind to or complex with the pro-PrP binding domain of FLNa. The pro-PrP regulating agent can include a peptide that has an amino acid sequence that is substantially homologous to about 5 to about 15 consecutive amino acids of a portion of the transmembrane GPI-PSS domain of pro-PrP that binds to FLNa. The transmembrane GPI-PSS of human pro-PrP has an amino acid sequence of GSSMVLFSSPPVILLISFIFLIVG (SEQ ID NO: 1). By "substantially homologous", it is meant the peptide has at least about 80%, about 90%, about 95%, about 96%, about 97%, about 98%, about 99% or about 100% sequence identity with a portion of the amino acid sequence of a portion of the transmembrane GPI-PSS domain of pro-PrP that binds to FLNa. In one example, the peptide can be substantially homologous to about 5 to about 10 consecutive amino acids of PPVILLISFLIFLIVG (SEQ ID NO: 2). In another example, the peptide can be substantially homologous to about 5 consecutive amino acids of FLIFLIVG (SEQ ID NO: 3). In yet another example, the peptide can be substantially homologous to the amino acid sequence FLIVG (SEQ ID NO: 4).

The competitive inhibitor of Pro-PrP can be modified by the mutation of one or more amino acid residues, by posttranscriptional modification, by posttranslational modification), such that the competitive inhibitor of the pro-PrP peptide retains the ability to inhibit the activity of the endogenous pro-PrP (e.g., binding of pro-PrP to FLNa).

It has been found that the non-polar amino acid residues of the FLNa binding domain of the GPI-PSS of pro-PrP are important in pro-PrP binding to FLNa. Therefore, in one particular aspect of the present invention, a purified polypeptide competitive inhibitor of pro-PrP can include the amino acid sequence $X_1LIX_2X_3IVG$ (SEQ ID NO: 5), wherein at least two of $X_1$, $X_2$, and $X_3$ are a neutral non-polar amino acid. In one example, at least one of $X_1$, $X_2$, and $X_3$ can be leucine or phenylalanine. In another aspect of the present invention, a purified polypeptide competitive inhibitor of pro-PrP can include the amino acid sequence VILLISX$_1$LIX$_2$X$_3$IVG (SEQ ID NO: 6), wherein at least two of $X_1$, $X_2$, and $X_3$ are a neutral non-polar amino acid (e.g., leucine or phenylalanine).

The competitive inhibitor of pro-PrP can also have other amino acid sequences that are substantially similar to pro-PrP GPI-PSS as long as the resultant polypeptide retains FLNa binding ability. For example, other competitive inhibitors can have an amino acid sequence of SEQ ID NO: 2, SEQ ID NO: 3, SEQ ID NO: 4, SEQ ID NO: 5, or SEQ ID NO: 6 but with deletions and/or substitutions that still allow the peptide to be a competitive inhibitor of pro-PrP.

It will be appreciated that the pro-PrP regulating agent can also include a peptide \ that has an amino acid sequence that is substantially homologous to about 5 to about 15 consecutive amino acids of a portion of the binding domain of FLNa that binds to pro-PrP and that inhibit binding of FLNa to pro-PrP in cancer cell expressing FLNa and pro-PrP.

The peptides and/or proteins of the present invention can also be modified by natural processes, such as post-translational processing, and/or by chemical modification techniques, which are known in the art. Modifications may occur anywhere in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other type of peptide modifications may include for example, amino acid insertion (i.e., addition), deletion and substitution (i.e., replacement), either conservative or non-conservative (e.g., D-amino acids) in the polypeptide sequence where such changes do not substantially alter the overall competitive inhibitor ability of the polypeptide.

Peptides and/or proteins of the present invention may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may promote axonal growth (without being restricted to the present examples).

The peptides and/or proteins of the present invention may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the peptides and/or proteins may be done by affinity methods, ion exchange chromatography, size exclusion chromatography, hydrophobicity or any other purification technique typically used for protein purification. The purification step can be performed under non-denaturating conditions. On the other hand, if a denaturating step is required, the protein may be renatured using techniques known in the art.

The peptides and/or proteins of the present invention can also be in the form of a conjugate protein or drug delivery construct having at least a transport subdomain(s) or moiety(ies) (i.e., transport moieties). The transport moieties can facilitate uptake of the peptides and/or proteins into a mammalian (i.e., human or animal) tissue or cancer cell. The transport moieties can be covalently linked to a peptides and/or proteins. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the polypeptide.

The transport moieties can be repeated more than once in the peptides and/or proteins. The repetition of a transport moiety may affect (e.g., increase) the uptake of the peptides and/or proteins by a desired cancer cell. The transport moiety may also be located either at the amino-terminal region of an active agent or at its carboxy-terminal region or at both regions.

In an aspect of the invention, the transport moiety can include at least one transport peptide sequence that allows the pro-PrP regulating agents to penetrate into the cell by a receptor-independent mechanism. By way of example, the transport moiety can include a cell penetrating pentapeptide with the amino acid sequence of KKRPK (SEQ ID NO: 7). It was found that KKRPK (SEQ ID NO: 7) has cell penetrating capacity and that the KKRPK motif (SEQ ID NO: 7) can be linked to a therapeutic peptide to facilitate entry of the therapeutic peptide into targeted cells. In one particular example, a cell-penetrating motif having the amino acid sequence of KKRPK (SEQ ID NO: 7) can be linked to the pro-PrP regulating agent comprising at least one of SEQ ID NO: 2, SEQ ID NO: 3, SEQ ID NO: 4, SEQ ID NO: 5, or SEQ ID NO: 6.

Additional examples of transport sequences that can be used in accordance with the present invention include a Tat-mediated protein delivery sequence (Vives (1997) 272: 16010-16017), polyargine sequences (Wender et al. 2000, PNAS 24: 13003-13008) and antennapedia (Derossi (1996) J. Biol. Chem. 271: 18188-18193). Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157 (Crisanti et al,) incorporated by reference in their entirety). Similarly, HIV Tat protein was shown to be able to cross cellular membranes (Frankel A. D. et al., Cell, 55: 1189).

In addition, the transport moiety(ies) can include polypeptides having a basic amino acid rich region covalently linked to an active agent moiety (e.g., pro-PrP regulating polypeptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. More preferably, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of the present invention can function as a transport agent region.

In another aspect of the invention, the pro-PrP regulating peptide agent can be non-covalently linked to a transfection agent. An example of a non-covalently linked polypeptide transfection agent is the Chariot protein delivery system (See U.S. Pat. No. 6,841,535; Morris et al. (1999) J. Biol.

Chem. 274(35):24941-24946; and Morris et al. (2001) Nature Biotech. 19:1173-1176), all herein incorporated by reference in their entirety.

The Chariot protein delivery system includes a peptide transfection agent that can non-covalently complex with the pro-PrP regulating polypeptide of the present invention. Upon cellular internalization, the transfection agent dissociates and the pro-PrP regulating agent is free to function. The complex of the Chariot transfection peptide and the pro-PrP regulating polypeptide agent can be delivered to and internalized by mammalian cells allowing for higher dosages of therapeutics to be delivered to the site of pathology. A molar excess of peptide transfection agent relative to the pro-PrP regulating polypeptide agent to be delivered can be employed to accomplish peptide transfection.

The pro-PrP regulating agent of the present invention can also include an agent that reduces or inhibits pro-PrP expression in cells to inhibit cell growth, cell proliferation, and motility. By "expression", it is meant the overall flow of information from a gene to produce a gene product (typically a protein, optionally post-translationally modified or a functional/structural RNA).

In another aspect of the invention, the pro-PrP regulating agent can include an RNAi construct that inhibits or reduces expression of PrP. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of, (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 5:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response. In such embodiments, the use of local delivery systems and/or agents, which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene or a particular family of genes, can be selected using methodology outlined in detail below with respect to the selection of antisense oligonucleotide. Similarly, methods of delivery RNAi constructs include the methods for delivery antisense oligonucleotides outlined in detail above.

In some embodiments, a lentiviral vector can be used for the long-term expression of a siRNA, such as a short-hairpin RNA (shRNA), to knockdown expression of pro-PrP in a cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of pro-PrP expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in $E\ coli$ strain DH5α cells. After positive clones are selected, plasmid can be transfected into 293T cells (A.T.C.C.) by calcium precipitation. The viral supernatant collected containing shRNA can then be used to infect mammalian cells in order to down regulate pro-PrP expression.

In another aspect of the invention, the pro-PrP inhibiting agent can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., pro-PrP).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an anomeric oligonucleotide. An anomeric oligonucleotide forms specific double-stranded hybrids with complementary RNA in which, contrary to the usual-units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

In a further aspect of the invention, the pro-PrP regulating agent can be expressed in the cancer cell being treated to inhibit cancer cell motility, migration, dispersal, and/or metastases. Gene therapy methods of transfecting cancer cells with vectors encoding the pro-PrP regulating agent can be readily employed to express and/or overexpress the pro-PrP regulating agent.

In some embodiments of the present invention, the pro-PrP regulating agent of the present invention can be provided in a pharmaceutical composition. The pharmaceutical compositions can include a pharmaceutically effective amount of a pro-Prp regulating agent described above and a pharmaceutically acceptable diluent or carrier.

The term "pharmaceutically acceptable carrier" "diluents", or "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount (dose) effective in treating a patient, having, for example, cancer, such as pancreatic ductal adenocarcinoma (PDAC). It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount of pro-PrP regulating agent to decreases the gene or expressed gene product of pro-PrP, suppress the functional activity of pro-PrP-FLNa binding in the cancer cells, and/or to inhibit cancer cell proliferation, motility, migration, dispersal, and/or metastasis.

Determination of a therapeutically effective amount is within the capability of those skilled in the art. The exact formulation, route of administration and dosage can be chosen by the individual physician in view of the patient's condition.

Pharmaceutical compositions of the present invention can be administered in a suitable pharmaceutical carrier by one of several routes that include systemic administration, (e.g., intravenous injection) parenteral administration, direct injection, and/or topical application. Formulations of the compositions will vary according to the route of administration selected (e.g., solution or emulsion).

In certain embodiments, the agent of the invention can be delivered to cancer cells by site-specific means. Cell-type-specific delivery can be provided by conjugating a therapeutic agent to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In an aspect of the invention, the agent described herein can be administered to a cancer cell, e.g., PDAC cell, of a subject by contacting the cell of the subject with a pharmaceutical composition described above. In one aspect, a pharmaceutical composition can be administered directly to the cell by direct injection.

In a further aspect of the invention, the agent can be used in combination and adjunctive therapies for inhibiting cancer cell proliferation, growth, and motility. The phrase "combination therapy" embraces the administration of a pro-PrP regulating agent in accordance with an aspect of the invention and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of the present invention.

A combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments the pro-PrP regulating agent can be administered in combination at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Another aspect of the present invention relates to diagnostic, prognostic, and therapeutic methods of detecting the level of pro-PrP in a patient's bodily sample to determine whether the subject has cancer and/or an increased risk of cancer. It was found that expression of pro-PrP in cancer cells can be associated with invasiveness, migration, and metastases of the cancer. Detection of pro-PrP in the cells of the cancer tissue and/or in blood, serum, or plasma of the subject can be used to determine whether the subject has cancer, the severity of the cancer, and/or the likelihood of cancer metastases.

Therefore, an aspect of the present invention relates to a method of detecting malignant progression of cancer cells in an animal is provided. The method includes the steps of: (1) obtaining a bodily sample from the subject (e.g., blood, serum, or plasma); (2) detecting the level of pro-PrP in the sample; and (3) correlating the level of pro-PrP in the sample to an increased risk of cancer in the subject and/or severity of the cancer in the subject.

Samples for use in the methods of the present invention may be obtained from the animal by various well known methods. The animal contemplated by the present invention can be a mammal. In particular aspects of the invention, the animal is a human. A sample obtained from an animal can refer to a biological sample, which includes, but is not limited to a tissue biopsy or section, blood sample, serum, plasma, lavage, swab, scrape, nipple aspirate, or other composition that may be extracted from the body and that contains suspected pro-PrP. In one particular aspect of the present invention, the bodily sample includes cancer cells, which express pro-PrP. In other aspects of the invention, the bodily sample includes blood serum or plasma obtained from the subject.

Certain aspects of the present invention include the step of detecting a level of pro-PrP in the sample obtained from the animal. The term "detecting" is used according to its ordinary and plain meaning to refer to "determining the presence of." In certain embodiments, pro-PrP is detected by assaying (measuring) a level or amount of pro-PrP in a given sample.

Methods of detecting a level pro-PrP can be achieved by techniques such as immunoprecipitations, Western blotting, ELISAs, other sandwich assays, FACS analysis and cross-linking assays. In these cases, antibodies may be used in a variety of detection techniques. It is understood that antibodies can be used to detect and to quantify polypeptides.

The level of pro-PrP detected in a sample can be correlated to the presence of cancer in subject, the increased likelihood of cancer in the subject, and/or severity of cancer in the subject. A subject that has a detectable circulating level of pro-PrP that is greater than the circulating level of pro-PrP in a normal subject can be indicative of the subject having cancer.

It is contemplated that one or more standards may be generated in which a normal level of pro-PrP in the subject or a tissue of the subject is defined or identified. That standard may then be referred to as a way of determining whether pro-PrP in a given sample taken from an animal is normal or above-normal. The type of standard generated will depend upon the assay or test employed to evaluate the presence or level of pro-PrP. In some embodiments of the invention, a score is assigned to a sample based on certain criteria and numbers within or above a certain number or range are deemed "above normal."

In some aspects of the invention, the level of pro-PrP is considered above normal if an assay indicates that a particular measurement, amount or level is at about or at most about 80%, 75%, 70%, 65%, 60%, 55%, 50%, 45%, 40%, 35%, 30%, 25%, 20%, 15%, 10%, 5% or greater than the measurement, amount or level observed in cells or samples that have normal levels of pro-PrP. In other words, for example, a subject with normal pro-PrP levels exhibits a level of pro-PrP that is x; the sample from the subject being tested may be 1.5x, in which case, in some embodiments that subject's sample may be considered to have an above normal level of pro-PrP.

Alternatively, in some aspects of the invention, the level of pro-PrP is considered above normal if an assay indicates that a particular measurement, amount or level is about or at least about 1, 2, 3, 4, 5, 6, 7, 8, 9, 10 or more standard deviations above the measurement, amount or level observed in subjects that have normal levels of pro-PrP. In other cases, the level of pro-PrP may be considered above normal if a measurement, amount or level indicative of pro-PrP is or is at most 2, 3, 4, 5, 6, 7, 8, 9, 10, 15, 20, 25, 30, 35, 40, 45, 50 or more times more than the measurement, amount, or level indicative of pro-PrP in a normal subject.

In some aspects of the present invention, increased levels of pro-PrP can be correlated to advanced degrees of tumor progression or even correlated directly to a specific tumor grade when compared to controls. In one example, a tumor grading system in which the level of pro-PrP may be correlated to is the World Health Organization grading system for astocytoma. The WHO system assigns a grade from 1 to 4, with 1 being the least aggressive and 4 being the most aggressive. It is contemplated by the present invention that a greater level of pro-PrP compared to a control sample will correspond to a more advanced tumor progression or even a higher or more malignant tumor grade.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

We investigated whether PrP is expressed in a group of 7 human pancreatic ductal adenocarcinoma (PDAC) cell lines, using a panel of well-characterized anti-PrP mAbs. We found that all 7 PDAC cell lines expressed PrP. However, the PrP in the PDAC cell lines was neither glycosylated nor GPI anchored. Rather, the PrP exists as a pro-protein retaining its GPI anchor peptide signal sequence (GPI-PSS). Unexpectedly, the GPI-PSS of PrP contains a filamin A-binding (FLNa-binding) motif. FLNa is a cytolinker protein. Binding of pro-PrP to FLNa disrupted the cytoskeleton and signaling events in the PDAC cell lines. Furthermore, in human pancreatic cancers, a subgroup of patient tumors expressed PrP, which correlated with markedly decreased survival. We found that binding of pro-PrP to FLNa confers pancreatic cancer with a growth advantage.

Cell Lines, mAbs, and Reagents

All 7 PDAC cell lines, BxPC 3, Panc 02.03, Capan 1, PL 45, CFPAC 1, Panc 1, and Panc 10.05, were obtained from ATCC. WV is a human neuroblastoma cell line that was originally generated in the laboratory of R. Petersen of Case Western Reserve University. Anti-PrP mAbs 8H4, 11G5, and 8B4 were generated in our laboratory. The rabbit anti-PrP GPI-PSS antiserum was generated by immunizing rabbits repeatedly with a synthetic peptide corresponding to the GPI-PSS of pro-PrP (GSSMVLFSSPPVILLISFIFLVG (SEQ ID NO: 1)) in CFA. The antiserum was affinity purified. All other mAbs and reagents were purchased from commercial sources and used according to the recommendations of the vendors. Mature PrP, pro-PrP, and PrP GPI-PSS GST fusion proteins were prepared using conventional techniques.

Immunofluorescence Staining for Confocal Microscopy

Tumor cell lines were cultured in poly-D-lysine-coated glass bottom Petri dishes (MatTek Corporation) overnight. Cells were then rinsed 3 times with ice-cold PBS and fixed in 4% paraformaldehyde for 15 minutes at 20° C. PrP or FLNa was detected with anti-PrP mAb 8H4 or anti-FLNa mAb PM6/317 (0.01 µg/µl). Bound Ab was detected with an Alexa Fluor 488 nm-conjugated (Invitrogen) goat anti-mouse Ig-specific antibody. Nuclei were stained with DAPI. To detect FLNa in PrP-downregulated cells, cells were fixed and then permeabilized with 0.3% Triton X-100 in PBS for 10 minutes at 20° C. The subsequent steps were carried out as described in above. F-actin was detected with Texas Red-conjugated (Invitrogen) phalloidin. Samples were analyzed on a LSM 510 META confocal microscope (Zeiss) at Case Comprehensive Cancer Center, Image Core Facility. All experiments have been repeated twice with comparable results.

Cell Lines, mAbs and Reagents

Capan-1 was cultured in Isocove's Modified Dulbecco's Eagle Medium (IMDM) supplemented with 1.5 g/L Sodium Bicarbonate and 20% fetal bovine serum (FBS). PL-45 was cultured in high glucose Dulbecco's Modified Eagle Medium (DMEM) supplemented with 1.5 g/L Sodium Bicarbonate and 10% FBS. Panc. 02.03 was culture in RPMI 1640 supplemented with 1.5 g/L Sodium Bicarbonate, 15% FBS, 1% Sodium Pyruvate, 1 mM Hepes, 20 U insulin, and 4.5 g/L Glucose. BxPC3 was cultured in RPMI1640 supplemented with 1.5 g/L Sodium Bicarbonate, 10% FBS, 1% Sodium Pyruvate, 1 mM Hepes, and 4.5 g/L Glucose. WV was cultured in RPMI 1640 supplemented with 10% FBS, 1% Sodium Pyruvate, 1 mM Hepes.

Anti-PrP mAbs 8H4 and 8B4 were generated in our laboratory and have been characterized extensively. Anti-CD55 mAb was purchased from BD Bioscience (San Jose, Calif.). Anti-FLNa A mAb, horseradish peroxidase (HRP) conjugated goat anti-human IgG Fc specific antibody and mouse anti-actin mAb were purchased from Chemicon (Temecula, Calif.). Anti-tyrosine-phosphorylated protein, anti-PAK, anti-phosphorylated PAK, anti-LIMK1, anti-LIMK2, anti phosphorylated LIMK1/2, anti-cofilin, anti-phosphorylated cofilin, and anti-chronophin antibodies were purchased from Cell Signaling Technology (Beverly, Mass.). Anti-CD55, Anti-ROCK1 and anti-ROCK2 antibodies were purchased from BD Biosciences (San Jose, Calif.). Fluorescein isothiocyanate (FITC)-labeled goat anti-mouse IgG antibody was purchased from Southern Biotech (Birmingham, Ala.). Texas red-conjugated phalloidin and 4',6-diamidino-2-phenylidole, dialactate, (DAPI) were purchased from Invitrogen (Carlsbad, Calif.). Protein G-agarose beads were purchased from Roche (Indianapolis, Ind.). PNGase F was purchased from New England BioLabs (Beverly, Mass.). Profound Co-Ip™ kit, EDTA-free protease inhibitor cocktail, dimethyl suberimidaet.2HCL (DMS) and SuperSignal®West Femto kit were purchased from Pierce (Rock, Ill.). Bio-Rad protein assay kit and silver stain plus kit were purchased from Bio-Rad (Hercules, Calif.). Phenylmethanesulfonyl fluoride (PMSF), Triton x-100, Tween-20, and phospholipase C (PI-PLC) were purchased from Sigma (St. Louis, Mo.). Carboxypeptidases B and Y were purchased from Worthington Biochemical Corporation (Lakewood, N.J.).

Flow Cytometry and Confocal Microscopy

To detect cell surface PrP in living tumor cell lines, cells were seeded in 25 cm$^2$ flask 12 hours before experiment, rinsed with ice cold DPBS once, and then released by treatment with Trypsin/EDTA. mAbs 8H4 or D7C7 (0.01 µg/µl) were then added to the cell suspensions at 4° C. After washing, bound antibody was detected by an Alexa Fluor 488 nm-conjugated goat anti-mouse Ig specific antibody and then analyzed in a BD FACS™ flow cytometer. To detect PrP or FLNa expression by confocal microscopy, tumor cell lines were cultured in poly-D-lysine-coated glass bottom Petri dish (MatTek, Ashland, Mass.) overnight. Cells were then rinsed 3× with ice cold DPBS and fixed in 4% paraformaldehyde for 15 minutes at 20° C. PrP or FLNa was detected with anti-PrP or anti-FLNa mAbs (0.01 µg/µl). Bound antibody was further detected with an Alexa Fluor 488 nm-conjugated goat anti-mouse Ig specific antibody. Nuclei were stained with DAPI. To detect FLNa in PrP down-regulated tumor cells, cells were fixed and then permeablized with 0.3% Triton X-100 in PBS for 10 minutes at 20° C. The other steps were carried out as described earlier. To detect change in tyrosine phosphorylated protein (p-tyr), tumor cells were prepared and treated as described in above, an anti-p-tyrosine antibody was added to the cells, and incubated overnight at 4° C. as suggested by the provider of the antibody. Bound antibody was detected with an Alexa Fluor 488 nm-conjugated goat an anti-mouse Ig antibody. Nuclei were stained with DAPI. F-actin was detected with a Texas Red-conjugated Phalloidin.

PI-PLC Treatment and Flow Cytometry Analysis of Live Cells

Tumor cells were seeded overnight as described. The next day, cells were first washed 3 times with ice-cold DPBS, and then treated with trypsin/EDTA to prepare a single cell suspension of the tumor cells. After washing twice with DPBS, cells were incubated with PI-PLC (500× dilution of 1 U) at 37° C. for one hour. At the end of the incubation, cells were washed twice with DPBS and then stained with control antibody or 8H4 as described.

For staining of live BxPC3 and Panc 02.03 cells with rabbit anti-PrP-GPI-PSS serum, single cell suspensions of the tumor cells were prepared as described and then incubated with either a rabbit non-immune serum (1:100) or affinity purified anti-PrP-GPI-PSS serum. An Alexa Fluor 488 nm conjugated donkey anti-rabbit antibody was used to detect bound rabbit antibody.

For staining of tumor cells with rabbit anti-PrP-GPI-PSS serum for confocal microscopy analysis, tumor cells were seeded overnight, washed 3 times with ice-cold DPBS, then fixed with 4% PFA for 15 minutes at 21° C. Subsequently, tumor cells were washed 3× with PBST, and then incubated with either the rabbit non-immune serum (1:100) or the affinity purified anti-PrP-GPI-PSS serum for 1 hour at 21° C. Bound primary antibody was detected with an Alexa Fluor 488 nm conjugated donkey anti-rabbit antibody.

Immunoblotting and Enzymatic Treatment of PrP from Various Tumor Cell Lines

Cell lysates were prepared in lysis buffer containing 20 mM Tris (pH7.5), 150 mM NaCl, 1 mM EDTA, 1 mM EGTA, 1% Triton X-100, 2.5 mM sodium pyrophosphate, 1 mM β-glycerolphosphate, 1 mM $Na_3VO_4$. 1 mM PMSF, and EDTA-free protease inhibitor cocktail was added just before cell lysis. PrP was affinity purified by mAb 8B4-conjugated beads, eluted and neutralized to pH 7.5. Purified PrP was subjected to carboxypeptidases or PNGase-F treatment followed by PI-PLC treatment according to the protocols provided by the providers. After treatment, samples were separated on SDS-PAGE and immunoblotted with an anti-PrP antibody. Briefly, 2 U PNGase F was added to 20 µl of eluted and neutralized PrP. 0.375 U PI-PLC was added to 20 ul PNGase F treated PrP. 1 U carboxypeptidases B or Y were added to 20 µl of eluted and neutralized PrP at 20° C. for different periods of time.

Sucrose Gradient Fractionation

Cell lysates prepared as described were mixed with an equal volume of ice-cold 80% sucrose in MES buffer [25 mM 2-(4-Morpholino) ethane sulfonic acid pH 6.5, 150 mM NaCl, 5 mM EDTA]. Two ml of 40% sucrose/cell lysate was transferred to a 5 ml Ultra-Clear centrifuge tubes (Beckman, Fullerton, Calif.) on ice. 2 ml ice-cold 30% sucrose in MES buffer was placed on top. 1 ml ice-cold 5% sucrose in MES buffer was loaded on the top of the gradient. Samples were centrifuged at 200,000×g for 16 hours at 4° C. 12×400 µl fractions were collected from top to bottom. 21 µl of each fraction was applied to 12% SDS-PAGE and then immunoblotted with anti-PrP, anti-flottlin-1 or anti-FLNa mAbs.

Immunoprecipitation, Immunoblotting, and Identification of Co-Purified Proteins by Mass Spectrometry To identify proteins that are normally bound to PrP in various tumor cell lines, cell lysates were prepared in Cell Signaling Co-I.P. Buffer (Cell Signaling Technology). Immunoprecipitation was performed with mAbs 8B4, 8H4, D7C7 or 1A10 that were conjugated to Sepharose beads. Beads were collected by centrifugation and washed extensively (×6) with PBS-T. Bound proteins were eluted using IgG-Elution Buffer (Pierce). The eluted proteins were then separated by SDS-PAGE (12% gel) and silver stained (Bio-Rad). One of the unique bands at 280 kDa was cut out, washed, reduced/alkylated, and digested with trypsin. The digested products were then analyzed by mass spectrometry at the Case Center for Proteomics, Mass Spectrometry Core Facility using a LC-MS system (Finnigan LTQ linear ion trap mass spectrometer). Identification of the protein was based on peptide fragment sequence homology with FLNa in the NCBI database, using the search program, Mascot. All matching spectra were further verified by manual interpretation. The interpretation process was aided by additional searches using the programs Sequest and Blast. To confirm that the protein bound to PrP$^C$ was FLNa, immunoprecipitated proteins were separated by 12% SDS-PAGE, electrotransferred to nitrocellulose membrane, and blotted with an anti-FLNa mAb. Bound antibody was detected with a goat anti-mouse-HRP antibody using the chemiluminescence blotting system (Pierce).

Binding of GST-PrP$^{23-253}$ to FLNa

2 μg of Flag-FLNa dimer or Flag-FLNa1-23 were mixed with 3 μg of GST-PrP231-253 in 400 μl binding buffer (20 mM Tris.HCl, pH7.4, 150 mM NaCl, 1 mM EGTA and 0.1% Tween 20), respectively. GST was used as control. The tubes were rocked slowly and incubated at RT for 1 hr. 10 μl of GST binding beads (Novagen, pre-equilibrated with binding buffer) was added and further incubated for 30 min. The beads were then washed with binding buffer ×5 (5 min/time). The beads were resuspended in 15 μl of 2×SDS loading buffer and boiled at 95° C. for 10 min. The proteins were separated on 4-20% Tris-glycine gel and then transferred to NC membrane. FLNa was detected with anti-Flag mAb (Sigma, 1:1000 dilution, 4° C. overnight). After second antibody incubation and washing, the membrane was developed by the addition of Supersignal West Femito Maximum sensitive substrate (Pierce, 1:20 dilution).

Binding to Pro-PrP 250 ng of Flag-FLNa was mixed with 1.2 μg of rPrP23-253 or rPrP23-230 in 400 μl binding buffer (same as above). The tubes were rocked slowly and incubated at RT for 1 hr. Then 3 μg of anti-PrP mAb 8H4 was added and incubated for another hour with gentle rocking. 10 μl of protein G agarose beads (pre-equilibrated with binding buffer) was then added for 30 min. The beads were washed with binding buffer for 5 min.×5. The beads were then resuspended in 15 μl of 2×SDS loading buffer and boiled at 95° C. for 10 min. The proteins were separated on a 4-20% Tris-glycine gel and then transferred to NC membrane. FLNa was detected with anti-Flag mAb (Sigma, 1:1000 dilution, 4° C. overnight). After second antibody incubation and washing, the membrane was developed as described above. On the same membrane, input rPrPs were detected with anti-PrP mAb 8B4.

Competition of Co-I.P. with Synthetic Peptide

BxPC-3 and Panc. 02.03 cell lysates were prepared as described in the co-i.p. experiment. mAb 8B4 conjugated beads were made as described by the provider (Pierce). Prior to the co-i.p. experiment, the efficiency of the beads was determined by direct immunoprecipitation of the cell lysate. For competition experiments, 400 μl of cell lysate from each cell type was loaded into the mAb 8B4 column. Synthetic peptides in the indicated amount were also added, as well as 4 μl of PMSF and 10 μl/column of DMSO. The columns were placed in the 4° C. cold room overnight with gentle rocking. Each column was then washed 6× with cell lysate buffer and eluted in 2×100 μl of Immunepure-IgG elution buffer (Pierce) in the cold room. Eluted proteins were separated in a 4-20% Tris-glycine gel, transferred to NC membrane and then immunoblotted with anti-FLNa mAb as described.

shRNA Down Regulation of PrP Expression

We first identified 3 sequences as potential targets of siRNA using OligoEngene™ software. The oligo sequences were first annealed and then ligated into linearized pSUPER RNAi vector (OligoEngene) (10:1) overnight at 4° C. The ligation product was further treated with Bgl II to reduce background and transformed into DH5α cells. Positive clones were selected after EcoRI and Hind III digestion showing the 281 bp band. Plasmid was then transfected into the 293T cell line (A.T.C.C.) by calcium-phosphate precipitation. Retroviral supernatant was collected 48 hrs later by filtering through a 0.45 μm filter. A shRNA with a "scrambled" sequence was generated identically and used as a control. The viral supernatant was used to infect PDAC cell lines for 6 hrs in the presence of 4 μg/ml polybrene. Culture mediums were then removed and replenished with fresh medium, and cells were allowed to recover for 24 hrs. Infected cells were selected with puromycin (2 μg/ml) for 48 hrs. Viable clones were expanded, and the levels of PrPC expression then quantified by immunofluorescence staining with anti-PrP mAbs followed by analysis by flow cytometry or by observation by a confocal microscopy or immunoblotting.

Cell Surface Biotinylation

PDAC tumor cells were surface incubated with sulfosuccinomidobiotin (Pierce) (0.1 mg/ml in labeling buffer (150 mM NaCl, 0.1 M Hepes, pH.8) for 30 min. After biotinylation cells were washed, lysed and immunoprecipitated with avdin conjugated beads in the co-immunoprecipitation buffer. Bound proteins were then eluted and immunoblotted with anti-PrP, anti-FLNa or anti-HSP90 mAbs. The flowthrough from the avidin-bead column, which contains the non-biotinylated cytosolic protein was also collected and then immunoblotted with the same mAbs.

ShRNA Knockdown of FLNa in Panc.02.03 Cells

Filamin A (human) "knock-down" and control scramble reagents were purchased from Santa Cruz Biotechnology (San Cruz, Calif.) and used as suggested by the provider.

Co-Localization of PrP and FLNa in Different Tumor Cells

Seeded tumor cells were first assayed for filamin A expression as described earlier. The cells were then blocked with normal mouse serum (1 mg/ml) for 1 hour at 20° C. PrP was then detected with biotinylated 8H4 (0.01 μg/μl) or biotinylated anti-CD55 (BD Biosciences) as control. Streptavidin Alexa Fluor 555 (Invitrogen) was applied to detect bound biotinylated antibodies. Nuclei were detected with DAPI.

Sandwich ELISA for Quantifying the Level of Soluble PrP in the Culture Supernatant of the PDAC Cell Lines One×$10^5$ of each PDAC cell line in 200 ml of culture medium was cultured in 96 well tissue culture plate (Corning, N.Y.) in triplicate. Twenty fours after culture, 100 ml of the culture medium was carefully removed. The level of soluble PrP present in the culture medium was then assayed using a sandwich ELISA as described by us. In this sandwich ELISA, mAb 8B4 was used as a capture-antibody and a biotinylated mAb 7A12 as used as a detecting antibody. The results presented represent the average of the triplicate well +/−S.E.

Immunohistochemical Staining

Unstained, 5 m sections were cut from paraffin blocks of selected cases and deparaffinized using standard techniques. Slides were treated with 1× sodium citrate buffer (diluted from 10× heat-induced epitope retrieval buffer; Ventana-Bio Tek Solutions, Tucson, Ariz.) before heating for 20 min. in a microwave oven. Slides were then cooled at room temperature for 20 min., and incubated with 3% w/v $H_2O_2$ for 10 min. Mouse anti-human PrP mAb, 8H4, was then added and incubated at room temperature for 1 hr. An isotype control mAb D7C7 was included in all experiments as a negative control. After serial washing, bound primary antibody was detected by adding a secondary antibody followed by avidin-biotin complex and 3,3'-diaminobenzidine (DAB) (Dako Inc, CA). Sections were counterstained with hematoxylin. Each slide was coded and evaluated by two pathologists (W. X and A. A. P.). The cytoplasmic and membrane staining intensity of each sample was graded as diffuse (>50% neoplastic cells stained positive), focal positive (5-50% neoplastic cells stained positive) or negative (<5% neoplastic cells stained). The identity of the case was revealed only after a score had been given. The process to detect GPI-SS of pro-prion protein in tumor sample was described above. Instead of 8H4, rabbit polyclonal antibody specific for the PrP GPI-PSS or non-immune serum was added and the second step antibody was a goat anti-rabbit Ig antibody.

In Vitro Proliferation

An identical number ($1 \times 10^4$) of cells were cultured in vitro in 24-well plates in triplicate. At different days after culture, the numbers of cells in each well were counted. The results presented were the mean of the triplicate wells ±SD at each time point. These results were confirmed with 3 independently generated control and PrP-downregulated cell lines.

In Vitro Invasion Assay

In vitro invasion assays were performed in the Bio-Coat Growth Factor Reduced Matrigel Invasion Chamber (BD Bioscience), using protocols provided by the supplier. The results presented were the mean of the triplicate wells ±SD. These results were confirmed with 3 independently generated control and PrP-downregulated cell lines.

Growth of Tumor Cells in Nude Mice

Tumor cells were grown in vitro to 90% confluence, washed twice in cold PBS buffer, harvested, washed with cold PBS 3 times, counted, and kept on ice prior to injection. Then, $1 \times 10^7$ cells in 0.1 ml of PBS were injected subcutaneously into the back of nude mice. In the BxPC 3 experiment, at 21 days after implantation, the tumor mass from each individual mouse was surgically removed and weighed. In the Panc 02.03 experiment, at various times after tumor cell implantation (5 mice/group/tumor cell line), the length and width of the tumors were measured using a digital caliper. The results presented were the mean of the weights of the tumors or the length×width$^2$/2 of the tumor ±SD. These results were confirmed with 3 independently generated control and PrP-downregulated cell lines.

Tissue Samples and Immunohistochemical Staining

Paraffin-embedded blocks of 83 surgically resected, primary infiltrating PDACs, were collected from the Surgical Pathology Files of University Hospital of Cleveland. Clinical and pathological data were obtained from detailed chart review, which included age, gender, race, tumor size, tumor location, lymph node metastasis status, and histological subtype of the invasive carcinoma. The H&E-stained slides from each case were visually inspected by light microscopy, and representative sections were selected for immunostaining.

Immunohistochemical staining of 5-µm sections was carried out using conventional methods. An isotype control, irrelevant mAb D7C7, and a nonimmune polyclonal rabbit antiserum were included as negative controls. Each slide was coded and evaluated independently by 2 pathologists (W. Xei and A. A. Petrolla.). The cytoplasmic and membrane staining intensity and distribution of each sample were graded as positive (>50% neoplastic cells stained strongly positive), weakly positive (5%-50% neoplastic cells stained weakly), or negative (<5% neoplastic cells stained). The identity of the case was revealed only after a score had been given. Similar results were obtained using 2 different anti-PrP mAbs 8B4 and 8H4. All studies have been approved by the Institutional Review Board for Human Investigation (UH IRB No. 08-05-29) of the University Hospital Case Medical Center, Cleveland, Ohio, USA.

Statistics

The frequencies of PrP immunostaining among normal pancreas, pancreatic precursor lesions, and cancer samples were analyzed by the $\chi 2$ test or Fisher's exact test to account for frequency values of less than 5. For purposes of statistical analysis, all PrP-positive carcinomas were combined for comparison to PrP-negative specimens. The Kaplan-Meier method was used to determine overall survival with respect to PrP expression. All 37 patients analyzed had surgery done in years from 2001 to 2003. None of these patients had presurgical chemotherapy or radiation therapy. P values of less than 0.05 were considered statistically significant.

PrP Exists as Pro-PrP in PDAC Cell Lines

Human PrP is synthesized as a 253-amino acid long pre-pro-PrP (FIG. 1). The N terminus has a leader signal sequence. The C terminus has the GPI-PSS. These sequences are removed in the ER and thus are absent from mature PrP. The protein backbone of mature PrP has a MW of about 23 kDa. Addition of 2 N-linked glycans and a GPI anchor completes the maturation of GPI-anchored PrP.

Figure 3:
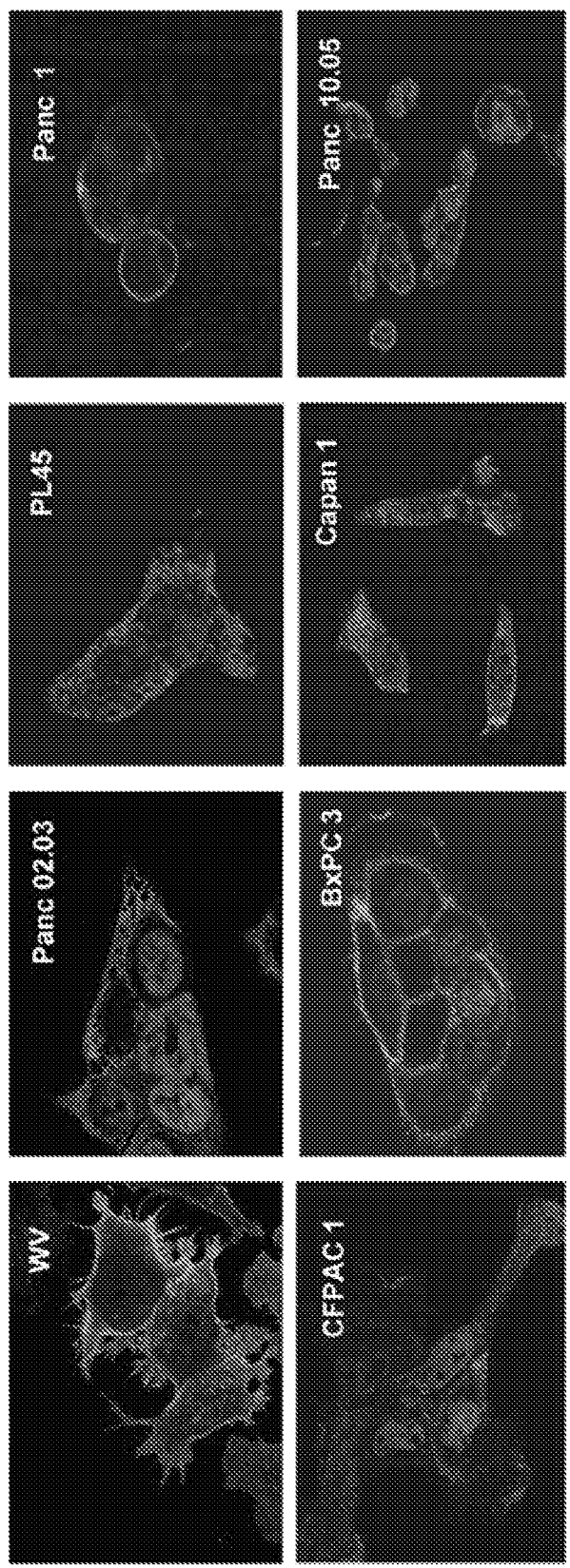
FIG. 3 illustrates confocal microscopic images showing that WV cells express PrP on the cell surface. All 7 PDAC cell lines express varying levels of PrP on the cell surface as well as in the cytoplasm. Original magnification, ×1,000.

When stained with a well-characterized anti-PrP mAb, 8H4, we found that PrP was expressed in a human neuroblastoma cell line, WV, as well as in a panel of 7 human PDAC cell lines which are as follows: BxPC 3, Panc 02.03, PL45, Capan 1, CFPAC 1, Panc 1, and Panc 10.05 (FIG. 3). While most of the PrP detected in WV cells was on the cell surface, in the human PDAC cell lines, PrP was detected on the cell surface and in the cytoplasm. The level of PrP varies among PDAC cell lines; BxPC 3 cells appeared to have highest level of PrP on the cell surface. The results of staining of live PDAC cell lines with mAb 8H4 supports this interpretation.

Figure 4:
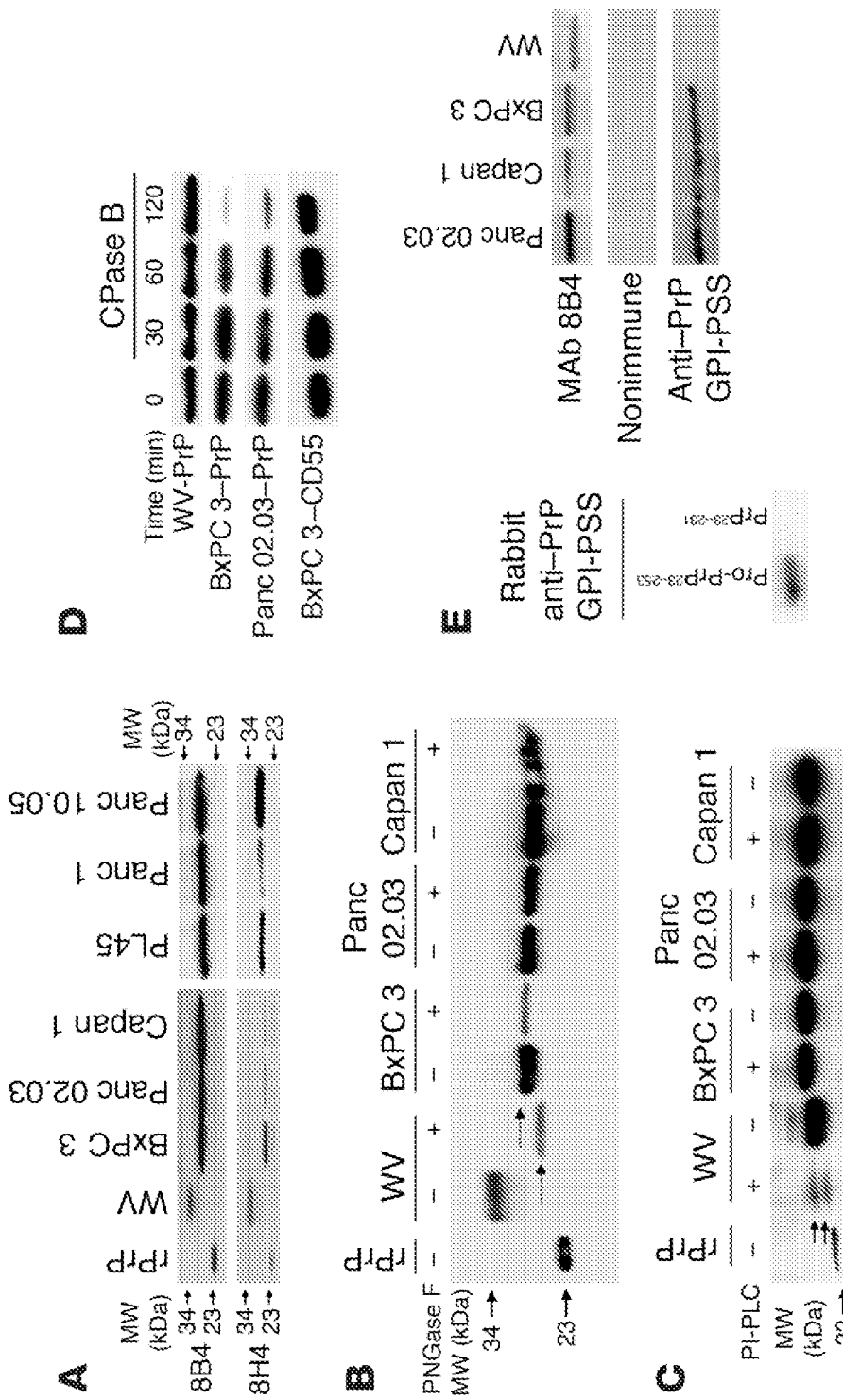
FIG. 4 illustrates (A) immunoblots showing PrP from WV cells has a Mol. Mass of 34 kDa, while PrP from the PDAC cell lines has a Mol. Mass of 26 kDa. A recombinant PrP (rPrP) produced in *E. Coli* is included as a control and Mol. Mass marker. (B) Immunoblots show treatment of PrP from WV cells with PNGase-F reduces its Mol. Mass from 34 kDa to 25.5 kDa. But identical treatment does not change the mobility of PrP from the PDAC cell lines. (C) Immunoblots show PrP from WV cells is sensitive to PI-PLC as shown by the appearance of a smaller PrP species, but PrP from the PDAC cell lines is resistant to PI-PLC. (D) Immunoblots show while PrP from the two PDAC cell lines is sensitive to carboxypeptidase B; PrP from WV cells is resistant. CD55 from BxPC3 cells is also resistant to carboxypeptidase B. (E) Immunoblots show a rabbit antiserum specific for the PrP GPI-PSS reacts with recombinant pro-PrP (rPrP$^{23-253}$) but not with mature PrP (rPrP$^{23-231}$). The anti-GPI-PSS antiserum also reacts with pro-PrP from the PDAC cell lines but does not react with the PrP from WV cells.

When immunoblotted with a N terminus-specific anti-PrP mAb 8B4 or a C terminus-specific anti-PrP mAb 8H4, PrP from WV cells migrated as a 33-34-kDa protein due to the addition of the N-linked glycans (FIG. 4). In contrast, PrP from the PDAC cell lines (n=6) migrated as a 26-kDa protein (FIG. 4). Because PrP from all 6 PDAC cell lines has similar MW, in subsequent studies we concentrated our studies on 3 of the PDAC cell lines: BxPC 3, Panc 02.03, and Capan 1.

To determine whether PrP in the PDAC cell lines contains N-linked glycans, we treated the cell lysates with endoglycosidase-F (PNGase F) prior to immunoblotting. Deglycosylation reduced the MW of PrP from WV cells from 34 kDa to 25.5 kDa (FIG. 4B). Identical treatment did not change the mobility of PrP from the PDAC cell lines. Hence, in the PDAC cell lines PrP is unglycosylated.

Deglycosylated PrP from WV cells migrated slightly faster than PrP from the PDAC cell lines (FIG. 4G). We therefore determined whether PrP is GPI anchored in the PDAC cell lines. Affinity-purified, deglycosylated PrP was treated with phosphatidylinositolspecific PLC (PI-PLC) to remove the GPI anchor prior to immunoblotting. After treatment, PrP from WV cells separated into 2 species, 25.5 and 25 kDa (FIG. 4C). In the 25-kDa PrP, the GPI anchor has been removed. This species represents 40%-60% of the total PrP in WV cells (n=3). The 25.5-kDa species is the deglycosylated PrP that is not cleaved by PI-PLC. Some GPI anchors are resistant to PI-PLC, due to the acylation of an inositol hydroxyl group in the anchor. Identical treatment did not change the mobility of PrP from the PDAC cells. Thus, PrP in these PDAC cell lines is either not GPI anchored or its GPI anchor is resistant to PI-PLC. This conclusion is consistent with our finding that treatment of live BxPC 3 and Panc 02.03 cells (data not shown) with PI-PLC did not reduce the level of cell surface PrP.

Carboxypeptidase (CPase) removes amino acids from the C termini of proteins. GPI-anchored proteins should be resistant to CPase, because their C termini are protected by the lipid anchors. If PrP from the PDAC cell lines lacks a GPI anchor, it should be susceptible to CPase. To test this hypothesis, affinity-purified, deglycosylated PrP from each cell line was treated for different periods of time with CPase B, prior to immunoblotting. As expected, PrP from WV cells was resistant to CPase B (FIG. 4D). However, after incubating with CPase B for 2 hours, the levels of PrP from BxPC 3 and Panc 02.03 cells were reduced by 80% (n=3). By contrast, CD55, another GPI-anchored protein in BxPC 3 cells, was resistant to CPase B. Furthermore, PrP from the PDAC cell lines but not PrP from WV cells was also sensitive to another CPase, CPase Y, which has distinct amino acid preference from CPase B (data not shown).

GPI-anchored proteins are present in lipid rafts. Because PrP in the PDAC cell lines lacks a GPI anchor, PrP is no longer detected in lipid rafts in BxPC 3 cells, while flotillin 1, a lipid raft residential protein, still remains in lipid rafts.

Based on the SDS-PAGE mobility of PrP from the PDAC cell lines, we speculate that PrP in the PDAC cells may still have its GPI-PSS. To test this hypothesis, we generated a polyclonal antiserum in rabbits that is specific for the GPI-PSS of PrP. The antiserum reacted with a recombinant pro-PrP$^{23-253}$, which contains the GPI-PSS, but not with a recombinant mature PrP$^{23-231}$, which lacks the GPIPSS (FIG. 4E). The antiserum also reacted with affinity-purified PrP from all 3 PDAC cell lines but not with affinity-purified PrP from WV cells (FIG. 4E). Pro-PrP is a precursor of mature PrP. The fact that no pro-PrP was detected in WV cells suggests that either the processing of PrP or the removal of the unprocessed pro-PrP is more rapid in WV cells. Collectively, these results provide conclusive evidence that in the PDAC cell lines PrP exists as pro-PrP.

Despite lacking a GPI anchor, some PrP was detected on the surface of PDAC cell lines. In general, the GPI-PSS contains 15-25 small, hydrophobic amino acids, similar to a typical transmembrane domain. Some cell surface PrP may represent pro-PrP, with its GPI-PSS inserted into the membrane; the GPI-PSS is functioning as a surrogate transmembrane anchor domain, a scenario that has been suggested by others. This hypothesis is consistent with our findings that 4 different anti-PrP mAbs, which reacted with epitopes spread along the PrP, reacted with cell surface PrP. Furthermore, while the anti-PrP GPIPSS antiserum reacted with fixed PDAC cells, it did not react with live PDAC cells. Therefore, on the cell surface the ectodomain of PrP is available to antibody binding but the GPI-PSS is not.

The PrP GPI-PSS Binds to FLNa

Figure 5:
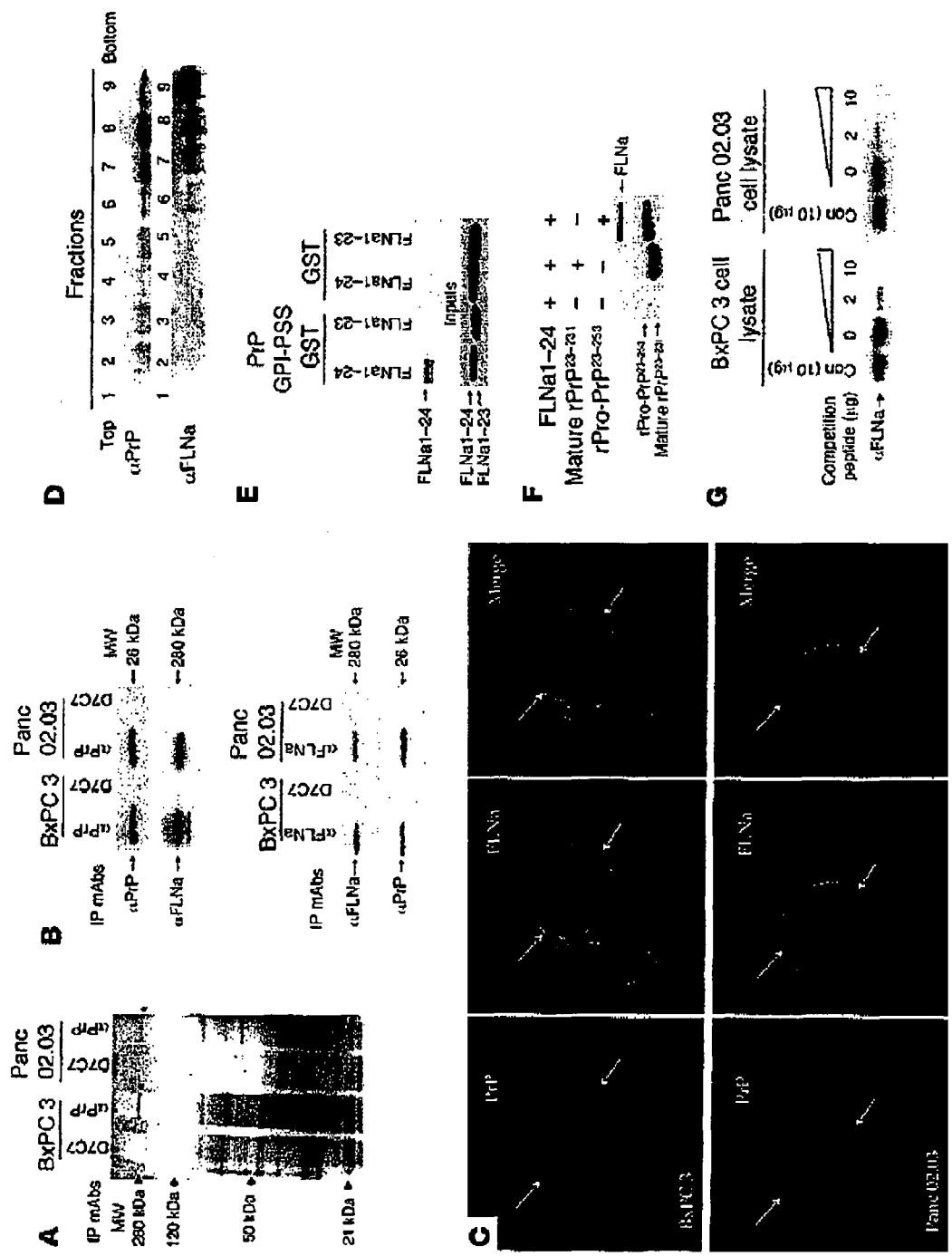
FIG. 5 illustrates FLNa binds to the GPI-SS of pro-PrP (A) A silver-stained gel shows a band with Mol. Mass of 280 kDa (*) is coimmunoprecipitated with mAb 8B4 but not with control mAb D7C7. (B) Immunoblots show the co-purification of FLNa with PrP and vice versa. (C) Confocal microscopic images show co-localization of FLNa and PrP in PDAC cell lines. (D) Immunoblots show PrP and FLNa are present in similar fractions after centrifugation in sucrose gradient. (E) An in vitro pull down experiment shows much stronger binding of full-length FLNa to a GST fusion protein, which has the PrP GPI-PSS. Immune complexes were pulled down with GST binding beads and immunoblotted with an anti-FLAG mAb to detect FLNa. (F) Immunoblots show binding of FLNa to pro-PrP but not mature PrP. Anti-PrP mAb 8H4 was used to pull down the immune complexes. The immunoblot was done either with an anti-Flag mAb or anti-PrP mAb 8H4. (G) Immunoblots show competition of binding of FLNa to pro-PrP by a PrP-GPIPSS synthetic peptide. Co-purification of PrP and FLNa in the PDAC cell lysates was carried out in the presence of different concentrations of either a synthetic peptide corresponding to the GPI-PSS (232-250) or a control "scrambled" synthetic peptide. Anti-PrP mAb 8B4 co-immunoprecipitated proteins were then immunoblotted with an anti-FLNa mAb.

We next sought to identify cellular proteins that interact with PrP in the PDAC cell lines. Coimmunoprecipitation with anti-PrP mAb 8B4 but not an irrelevant mAb D7C7 identified a prominent band with a MW of 280 kDa in BxPC 3 and Panc 02.03 cell lysates (FIG. 5A). The protein was sequenced by mass spectrometry and found to be FLNa, an actin-associated protein that integrates cell mechanics and signaling.

The identity of FLNa was confirmed by immunoblotting of proteins copurified with PrP with a FLNa-specific mAb (FIG. 5B). Conversely, immunoblotting of proteins copurified with FLNa with an anti-PrP mAb also revealed the presence of PrP (FIG. 5B). Furthermore, PrP and FLNa also partially colocalized in BxPC 3 and Panc 02.03 cells (FIG. 5C) and were present in similar fractions in a sucrose gradient (FIG. 5D). In WV cells, PrP did not co-purify with FLNa, because WV cells do not express FLNa (data not shown).

Native FLNa is a homodimer; each subunit contains a spectrinrelated F-actin-binding domain, followed by 24 Ig-like domains. Each Ig-like domain has about 96 amino acids and has 7 β-sheet strands (A to G). The faces of strands C and D are common binding sites for all FLNa-binding partners for which atomic structures have been resolved. These FLNa binding partners share a conserved, hydrophobic amino acid motif. Interestingly, ClustalW alignment suggests that the GPI-PSS of pro-PrP contains the FLNa-binding motif (Table 1). We thus investigated whether FLNa indeed binds the GPI-PSS of PrP.

TABLE 1

FLNa-binding motifs identified in known FLNa-binding partners

| Proteins | FLNa-binding motifs | SEQ ID NO. |
|---|---|---|
| GPIbα | - - F R S S L F L W V - - - | 10 |
| Integrin β$_1$ | - - Y K S A V T T V V - - - | 11 |
| Integrin β$_2$ | - - F K E A T T T V M - - - | 12 |
| Integrin β$_3$ | - - Y K E A T S T F T - - - | 13 |
| Integrin β$_7$ | - - Y K S A I T T T I - - - | 14 |
| DopD2R | - - T R T S L K Y M S - - - | 15 |
| DopD3R | - - L S T S L K L G P - - - | 16 |
| FilGAP | - - F S T F G E L T V - - - | 17 |
| Pro-PrP | V I L L I S F L I F L I V G$^{253}$ | 18 |

The table shows the alignment of known FLNa-binding motifs (49) and the presence of a potential FLNa-binding motif in PrP GPI-PSS. GPIbα, platelet glycoprotein Ib α polypeptide; integrin β$_1$, chain; DopD2R, dopamine D2 receptor1 FilGAP, GTPase-activating protein.

First, in an in vitro pull-down experiment, we found that a full-length FLNa1-24 dimer binds much more PrP GPI-PSS glutathione-S-transferase (GST) fusion protein than control GST protein without the PrP GPI-PSS. On the other hand, an FLNa1-23 monomer, which lacks the last Ig-like dimerization domain, did not bind the PrP GPI-PSS GST fusion protein (FIG. 5E). Second, this observation was confirmed by using full-length pro-PrP$^{23-253}$ and mature PrP$^{23-231}$, a full length FLNa dimer binds pro-PrP$^{23-253}$ but not mature PrP$^{23-231}$ (FIG. 5F). Third, these findings were further confirmed in BxPC 3 and Panc 02.03 cells. The levels of FLNa copurified with pro-PrP in these cell lines could be competed with a PrP GPI-PSS synthetic peptide, but not with a control peptide (FIG. 5G). Similar results were obtained with Capan 1 cells (data not shown). Together, these experiments provide strong evidence that FLNa binds to the GPI-PSS on pro-PrP.

PrP, but not FLNa, is readily detected in the membrane fraction when PDAC cell lysate was fractionated with a membrane protein extraction reagent kit (data not shown). Thus, PrP but not FLNa is embedded in the membrane. The high concentration of salts and detergent in the extraction buffer has probably prevented the co-fractionation of FLNa and PrP. We next determined whether FLNa, which is present near the inner membrane leaflet, interacts with membrane PrP as shown in FIG. 6. We labeled the cell surface of PDAC cell lines with biotin and then immunoprecipitated the biotinylated proteins with avidin-conjugated beads, using the coimmunoprecipitation buffer. Bound proteins were then eluted and immunoblotted with mAbs specific for PrP, FLNa, or Hsp-90. Hsp-90 is a cytosolic protein and is used as a control to determine whether contaminating cytosolic proteins are present in the cell surface protein preparation. It is clear that proteins bound to avidin beads contain PrP and FLNa but not Hsp-90. On the other hand, all 3 proteins were present in the flow through fraction, which includes cytosolic proteins (FIG. 7). In another series of experiments, we showed that PrP but not FLNa was readily biotinylated on the cell surface (data not shown). Collectively, these results suggest that FLNa interacts with cell surface PrP.

Downregulation of PrP Alters the Distribution of FLNa in PDAC Cell Lines

To study the possible consequences of the binding of pro-PrP to FLNa, we used shRNA to reduce PrP expression in the 3 PDAC cell lines. We identified 3 potential PrP-specific shRNA target sequences, and each shRNA was then introduced into BxPC 3, Panc 02.03, and Capan 1 cells to establish stable cell lines. As controls, stable cell lines expressing a scrambled shRNA-S were also established. One of the PrP-specific sequences, shRNA-10, inhibited the expression of PrP by more than 90%, as judged by immunofluorescent staining (FIG. 8A), immunoblotting (FIG. 8B), flow cytometry as well as by the amount of soluble PrP released by the tumor cells into the culture medium. Two other PrP-specific shRNA sequences, shRNA-2 and shRNA-4, inhibited the expression of PrP in BxPC 3 cells by 50% and 20%, respectively.

Reducing PrP does not Alter the Expression Levels of FLNa

Figure 8:
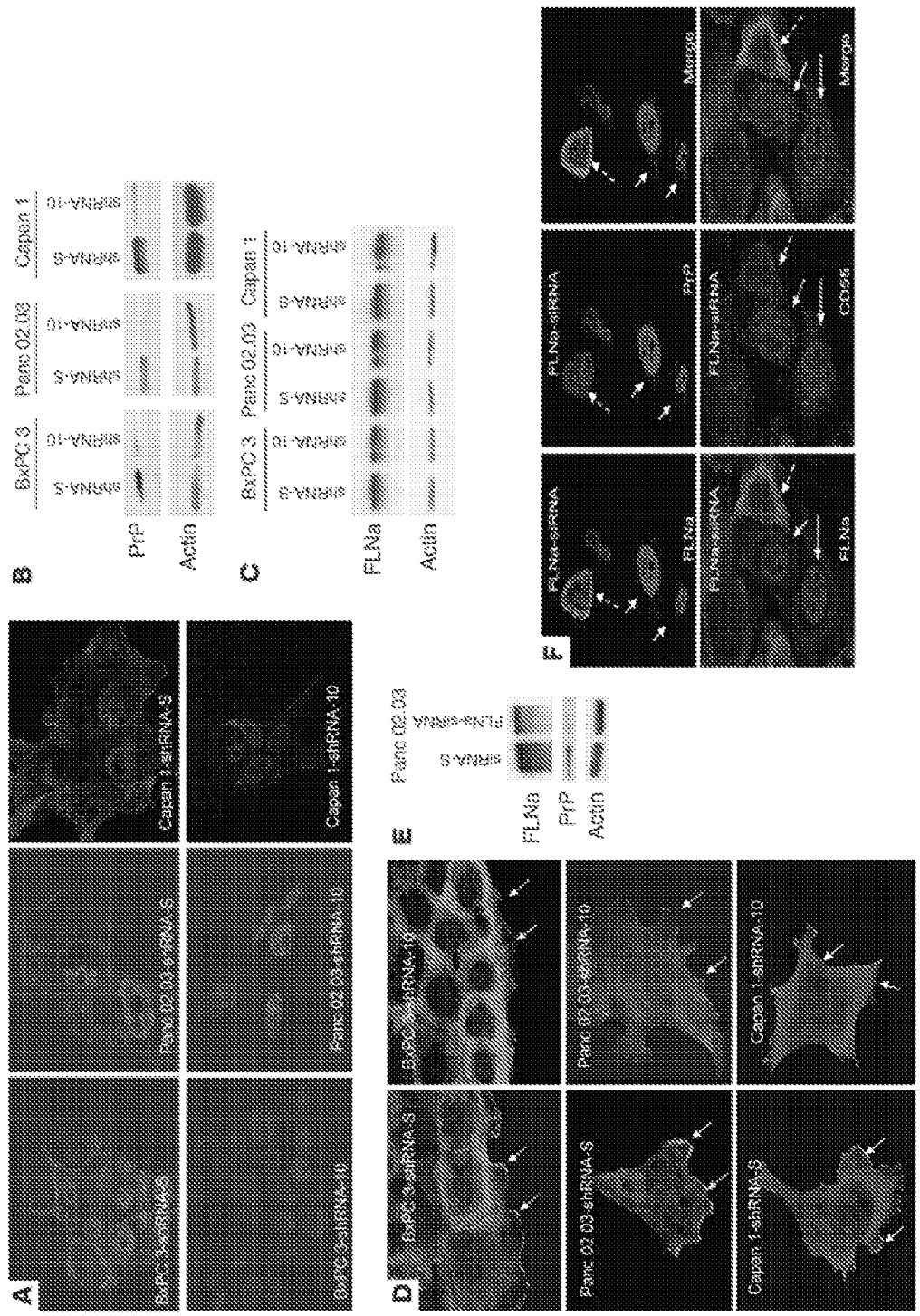
FIG. 8 illustrates down-regulation of PrP or FLNa expression in the PDAC cell lines (A) Immunofluorescence staining and confocal microscopic images show the PDAC cell lines with shRNA-10 have reduced levels of PrP. Original magnification ×1,000. (B) Immunoblots show the PrP down-regulated shRNA-10 cells have reduced levels of PrP. (C) Immunoblots show the level of FLNa does not change in PrP down-regulated cells. (D) Immunofluorescence staining and confocal microscopic images show that "knocking-down" PrP alters the spatial distribution of FLNa. (E) Immunoblots show that when expression of FLNa is inhibited the expression of PrP is also reduced in Panc 02.03 cells. (F) Immunofluorescence staining and confocal microscopic images show the expression of FLNa modulates PrP but not CD55 expression. Dash-arrow identified a cell with FLNa. Solid arrows identify two cells lacking FLNa (Top left panel). Two Cells lacking FLNa also lack PrP (Top center panel). Two FLNa negative cells still express high levels of CD55 (Bottom left and center panels).

The levels of FLNa in control cells and cells in which PrP has been downregulated (referred to herein as PrP-downregulated cells) are comparable (FIG. 8C). However, reducing PrP expression does alter the spatial distribution of FLNa. In control cells, FLNa is concentrated in areas lining the plasma membrane and membrane ruffles as well as diffusely in the cytosol (FIG. 8D, arrows indicate membrane ruffles). In the 3 PrP-downregulated cell lines, FLNa is greatly reduced in the membrane ruffles and is more concentrated in the cytosol. These results were confirmed in multiple independently established PrP-downregulated cell lines (n>3) and cell lines with scrambled shRNA-S (n>3).

Next, we used the approach of cell surface biotinylation to determine whether the amount of FLNa copurified with biotinylated cell surface protein is reduced in PrP-downregulated cells. It is clear that compared with control cells, the level of FLNa copurified with cell surface protein is markedly reduced in PrP-downregulated cells. Collectively, these results suggest that without PrP, much less FLNa is able to reach the inner membrane leaflet area.

Reducing FLNa Expression Diminishes the Expression of PrP

We were unable to establish stable FLNa knockdown PDAC cell lines. Therefore, we used siRNA to transiently reduce FLNa expression in Panc 02.03 cells. We achieved 60%-80% (n=3) reduction in FLNa expression (FIG. 8E); in these cells the level of PrP was also reduced (about 50%), as shown by immunoblotting (FIG. 8E). As shown by confocal microscopy, cells lacking FLNa also lacked PrP (FIG. 8F). On the other hand, cells that expressed FLNa also expressed PrP (FIG. 8F). This effect is specific for PrP, because cells lacking FLNa still have detectable CD55 (FIG. 8F).

Figure 9:
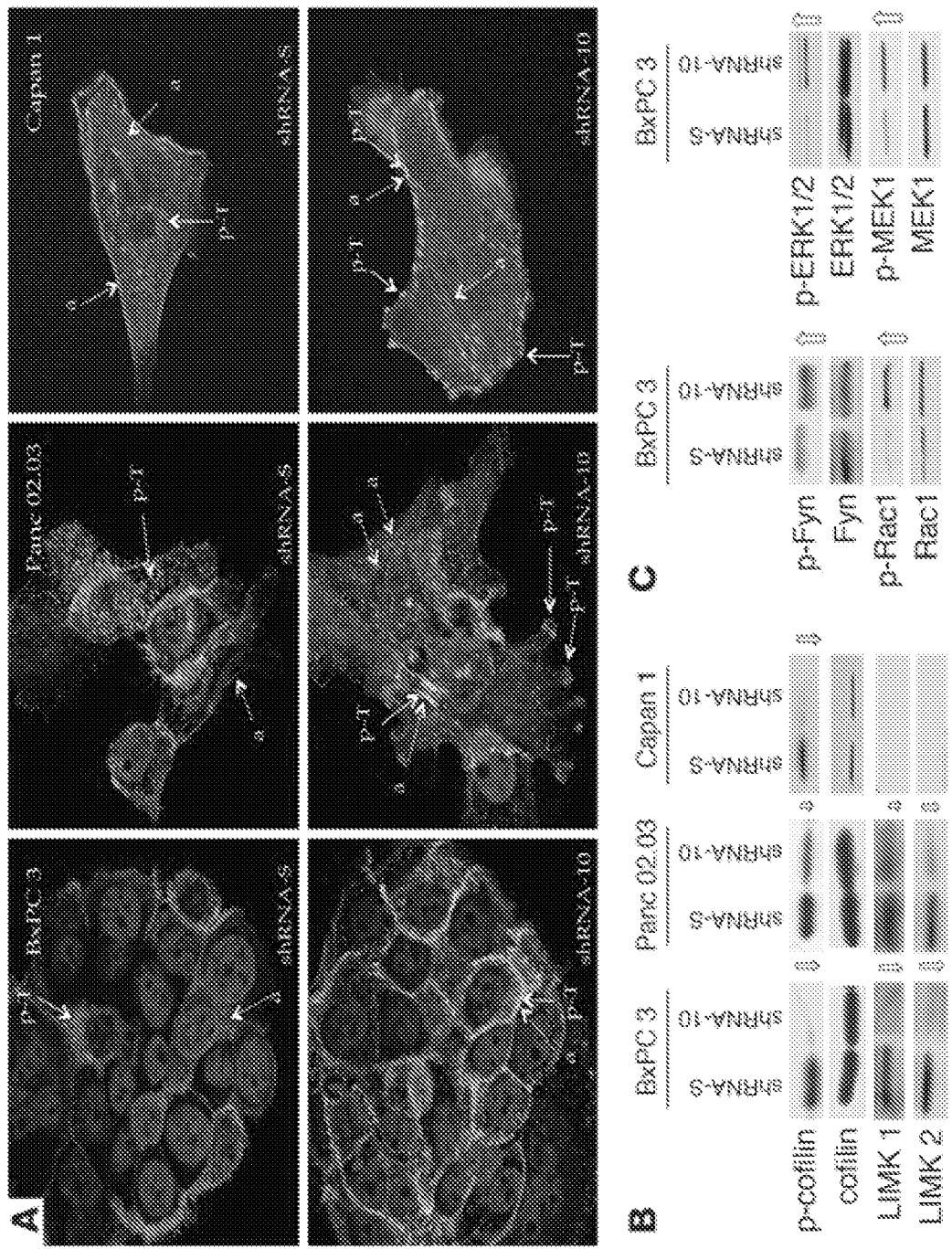
FIG. 9 illustrates binding of pro-PrP to FLNa alters actin organization and signaling events. (A) Immunofluorescence staining and confocal microscopic images show that "knocking-down" PrP modifies the spatial distribution of actin filaments and p-Tyr in three PDAC cell lines. (B) Immunoblots of PrP down-regulated BxPC 3 and Panc 02.03 cells show that the levels of p-cofilin, LIMK1 and LIMK2 are markedly reduced compared to control cells. P-cofilin is also reduced in PrP down-regulated Capan-1 cells. (C) Immunoblots show up-regulation of p-Fyn, p-Rac1, p-ERK1,2 and p-MEK1 in PrP down-regulated BxPC 3 cells

Downregulation of PrP Alters the Organization of Actin Filaments and Signaling Events in PDAC Cell Lines FLNa regulates actin polymerization and signaling. Therefore, we next stained control and PrP-downregulated cells for F-actin as an indicator of cytoskeletal organization. We also stained cells with an antibody specific for phosphorylated tyrosine, p-Tyr, as a generic indicator of signaling events. Downregulation of PrP drastically alters the staining patterns of both actin and p-Tyr in all 3 PDAC cell lines (FIG. 9A). In control BxPC 3 cells, actin and p-Tyr were mainly in the cytosol and tended not to colocalize. By contrast, in PrP-downregulated BxPC 3 cells, most of the actin and p-Tyr were colocalized in cell-cell contact areas. In control Panc 02.03 cells, actin was detected both in the cell membrane and in the cytosol, whereas p-Tyr was mainly in the cytosol. In PrP-downregulated Panc 02.03 cells, a more complex actin network was seen in the cytosol and in filopodia-like structures. In these cells, much of the p-Tyr was in the plasma membrane and colocalized with actin. Similarly, in control Capan 1 cells, most of the p-Tyr was in the cytosol. In contrast, in PrP-downregulated Capan 1 cells, most of the p-Tyr was in the plasma membrane, in a punctate pattern colocalized with actin. Thus, a reduction in PrP causes actin reorganization and alters signal transduction in all 3 PDAC cell lines, each with distinct phenotypes.

Cofilin regulates actin organization by controlling its polymerization. Two kinases, LIMK1 and LIMK2, phosphorylate and inactivate cofilin. This kinase activity is counteracted by a family of phosphatases, such as slingshot and chronophin, which dephosphorylate cofilin. We next determined whether changes in PrP levels modulate the levels of cofilin and p-cofilin in the PDAC cell lines. We observed that the levels of p-cofilin but not cofilin were reduced by 90%, 50%, and 90% in PrP-downregulated BxPC 3, Panc 02.03, and Capan 1 cells, respectively (FIG. 9B). The levels of LIMK1 and LIMK2 were also similarly reduced in PrP-downregulated BxPC 3 and Panc 02.03 cells. However, neither LIMK1 nor LIMK2 was detectable in Capan 1 cells. The levels of slingshot and chronophin were either unchanged or undetectable in these PDAC cell lines (data not shown). Hence, while the decrease in p-cofilin levels in BxPC 3 and Panc 02.03 cells can be explained by a reduction in LIMK1 and LIMK2, the upstream event that regulates p-cofilin in Capan 1 cells is not known.

In addition to cofilin, a large family of Rho-GTPases and kinases is involved in regulating cytoskeletal organization. We therefore investigated whether PrP influences the expression of some of the upstream signaling molecules in BxPC 3 cells. We observed that p-Rac1, a Rho-GTPase; p-ERK1/2 and p-MEK1, 2 serine/threonine kinases in the MAPK pathway; and p-Fyn, a Src family tyrosine kinase, are markedly increased in PrP-downregulated cells (FIG. 9C). Thus, PrP downregulation affects multiple signaling pathways in BxPC 3 cells.

PrP Modulates the Proliferation, Invasiveness, and Growth of PDAC Cell Lines

Figure 10:
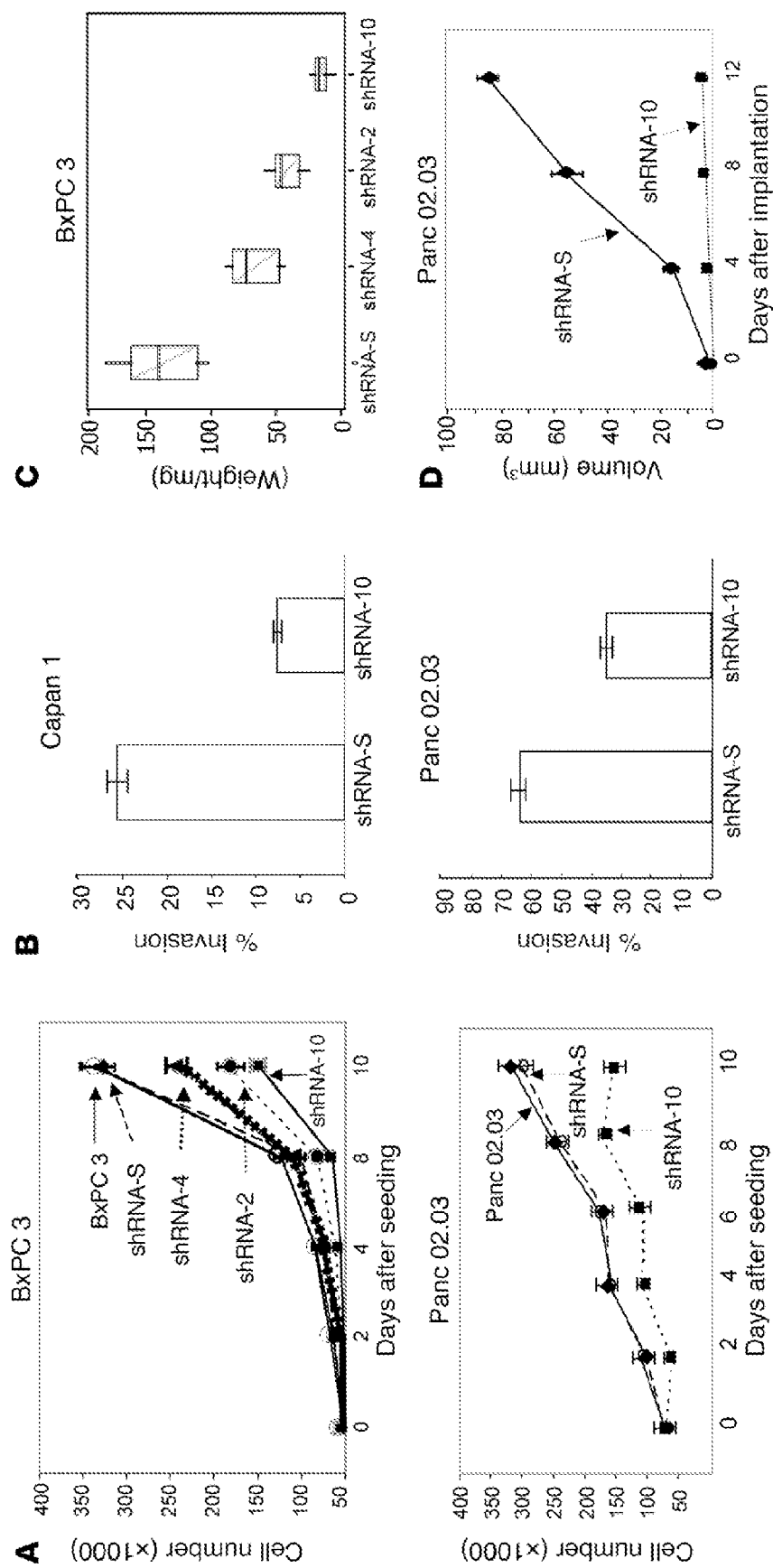
FIG. 10 illustrates down-regulation of PrP influences the in vitro and in vivo behavior of the PDAC cell lines (A) Proliferation of PrP down-regulated cells is reduced compared to control cells with scrambled shRNA-S or cells without any shRNAi. (B) In vitro invasiveness of PrP down-regulated Capan 1-shRNA-10 cells and Panc 02.03-shRNA-10 cells in Matrigel is reduced. The results presented are the means of triplicate wells. (C) In vivo growth of PrP down-regulated BxPC 3 cells in nude mice depends on the levels of PrP expression. (D) The growth of PrP down-regulated Panc 02.03-shRNA-10 cells in nude mice is inhibited. All these results were confirmed with three independently generated control and PrP down-regulated cell lines.

We next investigated the effects of knocking down PrP on PDAC cell behavior. PrP-downregulated BxPC 3-shRNA-10 and Panc 02.03-shRNA-10 cells proliferated more slowly than control cells with scrambled shRNA-S or control cells without any shRNA (FIG. 10A). The reduction in cellular proliferation correlates with the levels of PrP expression; BxPC 3-shRNA-10 cells, which expressed the lowest level of PrP, had the slowest proliferation rate, followed by BxPC 3-shRNA-2 cells, and then BxPC 3-shRNA-4 cells. PrP-downregulated Capan 1-shRNA-10 and Panc 02.03-shRNA-10 cells were also less invasive in vitro than control cells (FIG. 10B). We then inoculated nude mice with different PrP-downregulated BxPC 3-shRNA cell lines. Similar to that found for in vitro proliferation, BxPC 3-shRNA-10 cells also had the slowest growth rate, followed by BxPC 3-shRNA-2 cells, and then BxPC 3-shRNA-4 cells (FIG. 10C). When inoculated into nude mice, the growth of Panc 02.03-shRNA-10 cells was also retarded (FIG. 10D).

Pro-PrP is Detected in a Subgroup of Resectable Human PDAC Cases and Expression is Associated with Poorer Prognosis To determine whether our findings in cell models have clinical relevance, we carried out a retrospective study on the expression of PrP in human PDAC biopsies by immunohistochemistry. Tissues from patients with chronic pancreatitis or PanIN lesions served as controls. In normal human pancreas (FIG. 11, A-D), only islet cells (FIG. 11B) showed moderate PrP staining; neither acinar (FIG. 11C) nor ductal epithelial cells (FIG. 11D) stained for PrP. PrP was also undetectable in the duct cells in chronic pancreatitis (n=20), PanIN-1 (n=28) and PanIN-2 (n=40) (data not shown). Four of thirty (13.3%) PanIN-3 specimens showed weak staining for PrP (data not shown). Among the 83 resectable PDAC cases, 34 (41%) showed strong staining for PrP (FIG. 11) (summarized in Table 2).

TABLE 2

Summary of staining results

|  | Total Cases | PrP$^+$ cases |
| --- | --- | --- |
| Controls[A] | 20 | 0 |
| PanIN-1[B] | 28 | 0 |
| PanIN-2[C] | 40 | 0 |
| PanIN-3[D] | 30 | 4 (13%) |
| PDAC[E] | 83 | 34 (41%) |

[A]The 20 cases (11 males and 9 females) of controls had a mean age of 61.3 years.
[B]The mean patient age was 62.8 years (16 males and 12 females).
[C]The mean patient age was 63.5 years (22 males and 18 females).
[D]The mean patient age was 61.7 years (15 males and 15 females).
[E]The mean patient age was 63.2 years (49 males and 34 females).

Figure 11:
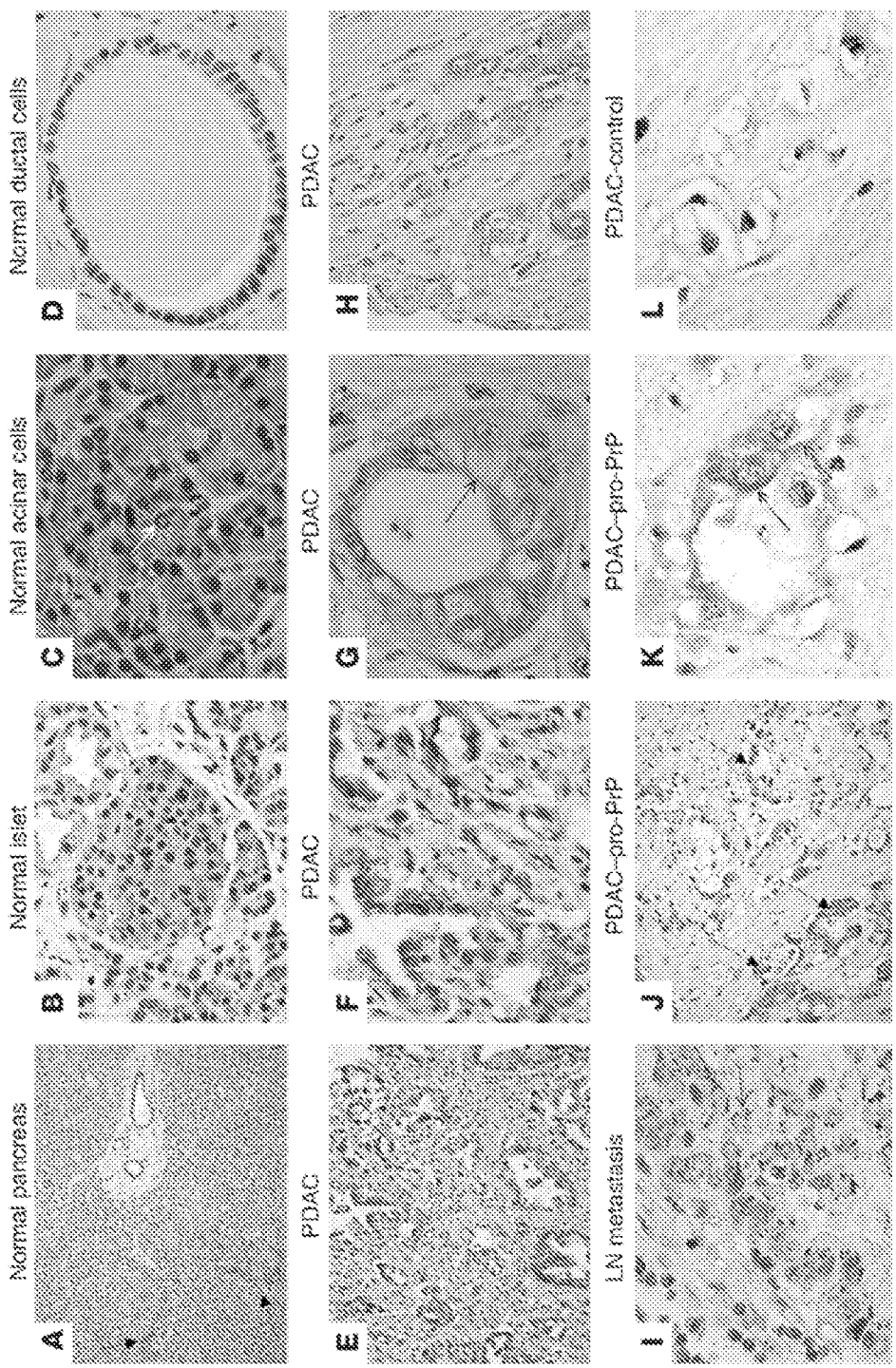
FIG. 11 illustrates PrP is present in PDAC lesions but not in normal ductal cells. Immunohistochemical staining shows that in normal pancreas (A-D) only islet cells express PrP. (A) Two arrows identify 2 islets (original magnification, x 100). (B) A PrP-positive islet (original magnification, x 400). (C) Neither acinar cells, an arrow shows a centroacinar cell (original magnification, x 400), nor (D) ductal cells (original magnification, x400) express PrP. (E-H) In PDAC, malignant ductal cells express PrP (original magnification, x200 [E]; x400 [H]). F and G are from 2 additional PDAC Patients (original magnification, x 400). (G) The dashed arrow shows immunoreactivity on the cell surface. (I) PDAC lymph node metastases express PrP (original magnification, x400). (J) PrP in PDAC reacted with the anti-PRP-GPI-PSS antibody; 3 arrows identify tumors (original magnification, x200). (K) Dashed arrows in K indicate PDAC cell surface immunoreactivity (original magnification, x 400). (L) The control antiserum only has background immunoreactivity (original magnification, x 400).

PrP immunoreactivity was also detected in the corresponding lymph node metastases (FIG. 7I). All PDAC tumor cells reacted strongly with the anti-GPI-PSS antiserum, but the stromal cells surrounding the tumor cells showed only background staining (FIGS. 11, J and K). The anti-GPI-PSS antiserum also failed to react with normal ducts in the same tissue biopsies. Staining of the PDAC with the control antiserum was also negative (FIG. 11L). Thus, as in the PDAC cell lines, PrP exists as pro-PrP in human PDAC lesions.

Figure 12:
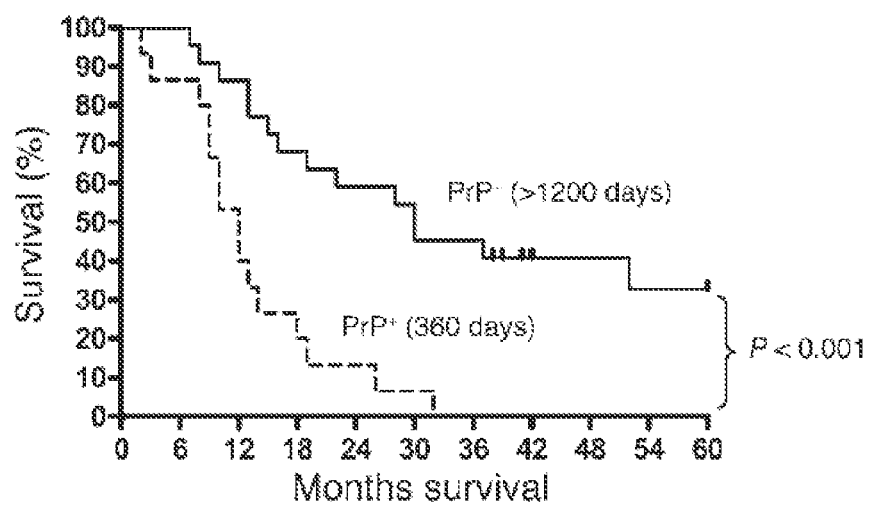
FIG. 12 illustrates the expression of PrP is associated with poorer prognosis The 37 patients had surgery done from 2001 to 2003. Patients (n=16) whose tumor expressed PrP had a medium survival time of 360 days. On the other hand, of the 21 patients, whose tumor lacked PrP, six of these patients are still alive as of October of 2008. Four of these patients have already passed 5 years after surgery; two others will have passed 5-year in late November of 2008 (two of the spikes). The other two spikes, one died 41 months and the other died 52 months after surgery. This cohort of patient has mean survival time of >1,200 days (P<0.001).

We next investigated whether PrP expression correlates with the clinical outcome in the group of 37 patients who had surgery done between 2001 and 2003. We observed that the expression of PrP is associated with shorter survival (FIG. 12). Patients (n=16) whose tumor showed strong PrP immunoreactivity had a shorter median survival time of 360 days, whereas patients (n=21) whose tumor did not show PrP immunoreactivity had a mean survival time of more than 1,200 days (P<0.001). Furthermore, we did not find any other factors, such as age, gender, tumor size, or differentiation, that are clearly associated with prognosis.

Example 2

We found that in human pancreatic ductal adenocarcinoma (PDAC) cell lines, PrP exists as pro-PrP retaining its GPI-PSS. Unexpectedly, The GPI-SS of PrP contains an FLNa binding motif. Binding of pro-PrP to FLNa modulates the cytoskeleton and signaling, providing a growth advantage to the PDAC cell lines. This defect appears to be specific for PrP, because the FLNa binding motif is only present on the GPI-PSS of PrP; it is absent on the GPI-PSS of 14 other normally GPI-anchored proteins. Furthermore, since CD55, which is normally a GPI-anchored protein, is GPI-anchored in the PDAC cell lines, therefore, the failure to remove the GPI-PSS is not due to a global defect in the GPI anchor machinery in the PDAC cell lines. Most importantly, about 40% of patients with pancreatic cancer express PrP in their cancer; these patients had significantly shorter survival compared to patients whose pancreatic cancers lack PrP. Collectively, these results suggest that the presence of pro-PrP provides a growth advantage to human pancreatic cancer cells.

Because the M2 and A7 melanoma cell lines represent a unique model for studying FLNa function, we investigated whether these cell lines express pro-PrP, and whether interaction between pro-PrP and FLNa is involved in their cellular behaviors. We found that both M2 and A7 cells express pro-PrP. More importantly, in A7 cells, FLNa does not act alone; it is the interaction between pro-PrP, integrin β1 and FLNa that controls cell spreading and migration. A model is proposed to account for these observations.

Cell Lines and Reagents

The generation, characterization and culture of the melanoma cell lines, M2 and A7 have been described. All the anti-PrP mAbs with the exception of SF34, were generated, characterized and affinity purified in our laboratory. SF34 was kindly provided by Dr. Jacues Grassi of Service de Pharmacologic et d'immunologie, CEA/Saclay, Gil sur Yuette, France. Mature PrP$^{23-231}$, pro-PrP$^{23-253}$ and pro-PrP, in which the polar amino acids residues in the GPI-PSS were replaced with non-polar amino acids residues as well as various GPI-PSS deletion mutants were prepared using conventional molecular biological techniques as described by us. Anti-FLNa A mAb and mouse anti-actin mAb were purchased from Chemicon. Anti-LIMK1, anti-p-LIMK1, anti-LIMK2, anti-p-LIMK2, anti-cofilin, anti-p-cofilin, anti-calnexin antibodies were purchased from Cell Signaling Technology. Anti-FAK, anti-p-FAK (Tyr 576,577), anti-Src, and anti-p-Src (Tyr529) monoclonal antibodies were purchased from Santa Cruz Biotechnology. Fluorescein isothiocyanate (FITC)-labeled goat anti-mouse IgG antibody was purchased from Southern Biotech. Texas red-conjugated phalloidin and 4',6-diamidino-2-phenylidole, dialactate, (DAPI), BODIPY F-05 ceramide BSA complex were purchased from Invitrogen. Protein G-agarose beads were purchased from Roche. Profound CO-IP kit, EDTA-free protease inhibitor cocktail, dimethyl suberimidaet.2 HCL (DMS) and SuperSignal®West Femto kit were purchased from Pierce. Bio-Rad protein assay kit was purchased from Bio-Rad. Phenylmethanesulfonyl fluoride (PMSF), Triton x-100, Tween-20, brefeldin A (BFA), and phospholipase C (PI-PLC) were purchased from Sigma. Streptavidin-Agarose beads were purchased from MP Biomedicals.

Immunofluorescent Staining for Confocal Microscopic Studies

Tumor cell lines were cultured in poly-D-lysine-coated glass bottom Petri dishes (MatTek) overnight. Cells were then rinsed 3× with ice cold PBS and fixed in 4% paraformaldehyde for 15 min at 20° C. PrP or FLNa was detected with anti-PrP mAb 8H4 or anti-FLNa mAb PM6/317 (0.01 µg/µl). Bound antibody was detected with an Alexa Fluor 488 nm-conjugated goat anti-mouse Ig specific antibody. For pro-PrP staining, cells treated similarly were stained with a 1:100 dilution of the affinity purified rabbit anti-PrP-GPI-PSS antiserum. Bound rabbit antibody was detected with an Alexa Fluor 488 nm-conjugated goat anti-rabbit Ig specific antibody. Nuclei were stained with DAPI. F-actin was detected with Texas Red-conjugated phalloidin. Samples were analyzed on a LSM 510 META confocal microscope at The Case Comprehensive Cancer Center, Image Core Facility.

Flow Cytometry

To detect cell surface PrP in tumor cell lines, cells were seeded in 25 cm² flask 12 hours before experiment, rinsed with ice cold DPBS once, and then released by treatment with Trypsin/EDTA. Anti-PrP mAbs, anti-integrin β1 mAb or control, irrelevant mAb D7C7 (0.01 µg/µl) were then added to the cell suspensions at 4° C. After washing, bound antibody was detected by an Alexa Fluor 488 nm-conjugated goat anti-mouse Ig specific antibody and then analyzed in a BD FACS flow cytometer.

PI-PLC Treatment and Flow Cytometry Analysis of Live Cells

Tumor cells were seeded overnight as described. The next day, tumor cells were first washed 3 times with ice-cold DPBS, and then treated with trypsin/EDTA to prepare a single cell suspension of the tumor cells. After washing twice with DPBS, cells were incubated with PI-PLC (100× dilution of 1 U) at 37° C. for one hour. At the end of the incubation, cells were washed twice with DPBS and then stained with control antibody or 8H4 as described. All samples were then analyzed in a BD FACS flow cytometer.

Immunoblotting and Enzymatic Treatment of PrP

Cell lysates were prepared in lysis buffer containing 20 mM Tris (pH7.5), 150 mM NaCl, 1 mM EDTA, 1 mM EGTA, 1% Triton X-100, 2.5 mM sodium pyrophosphate, 1 mM β-glycerolphosphate, 1 mM $Na_3VO_4$. 1 mM PMSF, and EDTA-free protease inhibitor cocktail was added just before cell lysis. PrP was affinity purified by mAb 8B4-conjugated beads, eluted and neutralized to pH 7.5 as described. Purified PrP was subjected to PNGase-F treatment according to the protocols provided by the provider (two U PNGase F was added to 20 µl of eluted and neutralized PrP). After treatment, samples were separated on SDS-PAGE and immunoblotted with an anti-PrP mAb.

Immunoblotting of Proteins that are Co-Purified with PrP, FLNa or Integrin β1

To identify proteins that are bound to PrP, cell lysates were prepared in Cell Signaling Co-I.P. Buffer (Cell Signaling Technology) Immunoprecipitation was performed with anti-PrP mAb 8H4 or control, irrelevant mAb D7C7 that were conjugated to Sepharose beads. Beads were collected by centrifugation and washed extensively (×6) with PBS-T. Bound proteins were eluted using IgG-Elution Buffer (Pierce). The eluted proteins were then separated by SDS-PAGE (12% gel) and then immunoblotted with anti-FLNa mAb or anti-integrin β1 mAb. Bound antibody was detected with a goat anti-mouse-HRP antibody using the chemiluminescence blotting system (Pierce). Similar approaches were used to determine whether FLNa co-purifies with integrin β1 using anti-integrin β1 mAb.

Binding of Individual FLNa Domains to Pro-PrP

All the recombinant FLNa proteins and the individual FLNa domains were prepared as described. In in vitro pull-down experiments, 250 ng of GST-tagged FLNa was mixed with 1.2 µg of rPrP23-253 or rPrP23-230 in 400 ul binding buffer (20 mM Tris.HCl, pH7.4, 150 mM NaCl, 1 mM EGTA and 0.1% Tween 20). The tubes were rocked slowly and incubated at RT for 1 hr. Then 3 µg of anti-PrP mAb 8H4 was added and incubated for another hour with gentle rocking. 10 µl of protein G agarose beads (pre-equilibrated with binding buffer) was then added for 30 min. The beads were washed with binding buffer for 5 min.×5. Subsequently, beads were resuspended in 15 µl of 2×SDS loading buffer and boiled at 95° C. for 10 min. The proteins were separated on a 4-20% Tris-glycine gel, and then transferred to NC membrane. FLNa was detected with anti-GST tag mAb (Sigma, 1:1000 dilution, 4° C. overnight). After second antibody incubation and washing, the membrane was developed as described above. On the same membrane, input rPrPs were detected with anti-PrP mAb 8B4.

In Silico Modeling of FLNa Domain 23 Bound to GPI-PSS Peptide

The complex of FLNa23 with bound PrP GPI-PSS-peptide was modeled with HOMODGE in BODIL, by using FLNa21 with bound integrin β7 peptide (pdb-code: 2brq2) as a template structure. Intra-molecular and inter-molecular interactions at the interaction areas between FlnA23 and bound PrP GPI-PSS peptide were optimized by using side-chain rotamer library, incorporated within BODIL.

Competition of Co-I.P. with Synthetic Peptide

For competition experiments, 400 µl of cell lysate from each cell type was loaded into the mAb 8B4 column. Since the PrP-GPI-PSS is rather insoluble, a KKRPK motif was added to the N-terminus of the PrP-GPI-PSS to increase is solubility. Control peptide also has the KKRPK motif followed by 21 irrelevant amino acids (for peptide sequences see wound-healing assay). Synthetic peptides in the indicated amount were also added, as well as 4 µl of PMSF and 1 µl/column of DMSO. The columns were placed in the 4° C. cold room overnight with gentle rocking. Each column was then washed 6× with cell lysate buffer and eluted in 2×100 µl of Immunepure-IgG elution buffer (Pierce) in the cold room as described by us. Eluted proteins were separated in a 4-20% Tris-glycine gel, transferred to NC membrane and then blotted with anti-FLNa mAb as described.

Down Regulation of PrP Expression by shRNA

For inducible system, we used BLOCK-iT$^T$ inducible H1 lentiviral RNAi system (Invitrogen) to generate PrP down regulated M2 or A7 cell lines by following manufacturer's guideline. The sequences of shRNA-10, shRNA-12, shRNA-3 from the PRNP gene have been described previously. In brief, M2 and A7 cells were transfected with pLENTI6/TR plasmids by using jet PEI cationic polymer transfection reagent (Polyplus Transfection In). Forty-eight hrs after transfection, 5 µg/ml of blasticitin was added to the medium to select for stable cell line. Tetracycline repressor (TetR) expression was detected by immunoblotting with anti-TetR antibody (MoBiTec). The established TetR-expression host cell lines were kept in medium supplemented with 2.5 µg/ml of blasticitin. The oligonucleotides, shRNA-10, shRNA-12 and shRNA-3, were annealed and cloned into pENTER/H1/TO vector by ligation overnight at 4° C. Positive clones were confirmed by sequencing. The ready pENTER/H1/TO constructs were then transfected into M2 and A7 TetR-expression host cell lines with jet PEI reagent respectively. After selection with 500 µg/ml of zeocin in medium, viable clones were expanded, and induced with 1 µg/ml deoxycycline in medium for 5 to 7 days. PrP expression levels were quantified by immunoblot with anti-PrP mAbs. At least three independently generated clones from each shRNAi sequence were studied.

Spreading Assay

To study the effects of PrP knock down on cell spreading, single suspension of PrP down regulated and control cells were seeded in a 24 well tissue culture plate in triplicate and cultured for 2 hours. The cells were then counted in a Zeiss Axiovert microscope. To study peptide effects on cell spreading, cells were culture with the PrP GPI-PSS synthetic peptide, KKRPK-PPVILLISFLIFLIVG (Peptide2, Chantilly, Va.) (SEQ ID NO: 8) or a control peptide, KKRPK-DMDYLPRVPN-QGIIINPMLSD (Peptide2) (SEQ ID NO: 9) overnight at specified concentration. After that, single cell suspensions were prepared, and counted. Same numbers of cells were plated in 24 well tissue culture plates in triplicate. Thirty minutes later, the numbers of cells with adherent morphology, or in suspension in each well were counted in a Zeiss Axiovert microscope. The results presented were the mean of the triplicate wells +/−S.E.

Wound Healing Assay

The tumor cells were seeded and allowed to grow until confluent in triplicates. A wound was inflicted by scraping across the cell layer with a 200 µl sterile peptide tip. The cells were incubated for various lengths of time followed by imaging at 10 on a Zeiss Axiovert 200 microscope equipped with an AxioCam digital camera system. Average wound area was quantified in the picture using ImageJ software (means+/−standard deviation of the triplicates) Inhibition of cell migration was determined by comparing with the healed area of non-treated cells with the healed areas of cells treated either with various concentrations of the PrP-GPI-PSS synthetic peptide, KKRPK-PPVILLISFLIFLIVG (SEQ ID NO: 8) (Peptide2) or a control, irrelevant synthetic peptide, KKRPK-DMDYLPRVPNQGIIIN-PMLSD (SEQ ID NO: 9) (Peptide2). All peptides were added right after the creation of the wound. Percent inhibition of wound healing was calculated: 100×(1−healed area of treated cells/healed area of non-treated cells).

In M2 and A7 Cells PrP Exists as Pro-PrP

As expected, FLNa is detected in A7 cells but not in M2 cells (FIG. 13A). On the other hand, both M2 and A7 cells express PrP. In immunoblots, a normal, glycosylated, GPI-anchored PrP has a molecular mass of about 34 KDa. In contrast, PrP from M2 and A7 cells migrates as a 26 KDa protein (FIG. 13A).

PrP is present on the cell surface of M2 and A7 cells at comparable level, as judged by immunofluorescent staining of live M2 and A7 cells with multiple anti-PrP mAbs, which react with epitope spread along the PrP (FIG. 13B, for epitopes of the mAbs). Subsequently, we found that in M2 and A7 cells, PrP is neither glycosylated nor GPI-anchored, it exists as pro-PrP, as in pancreatic cancer cells. This conclusion is based on the following: 1) treatment with endoglycosidase-F (PNGase-F) did not alter the motility of PrP from M2 and A7 cells in SDS-PAGE; 2) PrP on M2 and A7 is resistant to phospholipase C (PI-PLC); 3) a polyclonal antiserum that is specific for the GPI-PSS of PrP reacts with affinity purified PrP from M2 and A7 cells.

Figure 13C:
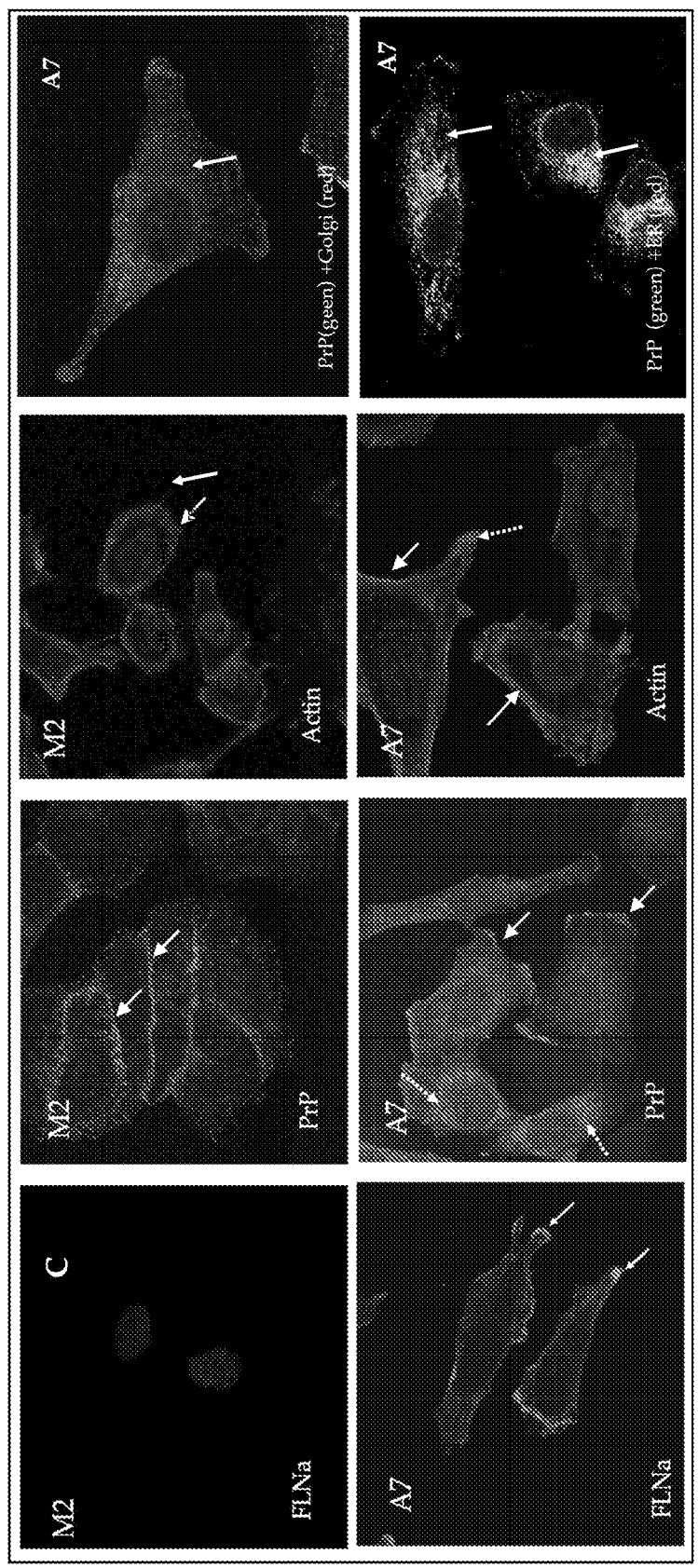
FIG. 13 illustrates the expression of FLNa and pro-PrP in M2 and A7 melanoma cell lines. (A) Immunoblots show that only A7 cells express FLNa, but pro-PrP is expressed in both M2 and A7 cells. PrP from M2 and A7 cells migrate as a 26 kDa protein as revealed by immunoblotting with either mAb 8H4, which reacts with an epitope at the C-terminus or with mAb 8B4, which reacts with an epitope at the N-terminus. A bacterial produced recombinant mature PrP$^{23-231}$, which lacks N-linked glycans, the GPI-PSS and the GPI anchor, (M-PrP) and a recombinant pro-PrP$^{23-253}$, which contains the GPI-PSS (pro-PrP) were included as molecular weight markers. Pro-PrP from A2 and M7 cells migrate a bit slower than a recombinant pro-PrP produced in bacteria. This most likely reflects the conformational difference between recombinant pro-PrP and native pro-PrP. Bacterially produced pro-PrP is insoluble, and has to be solublized, and refolded in urea, which might caused the protein to be more compacted. (B). Histograms show that on the cell surface of M2 and A7 cells PrP reacts with multiple anti-PrP mAbs with epitopes spread along the PrP molecule. Staining with mAb 8B4 was significantly lower than all other anti-PrP mAbs, because the epitope of mAb 8B4, which is located at the N-terminus, is sensitive to trypsin. Trypsin was used to prepare the single cell suspension required for flow cytometry staining. (C). Photographs of confocal microscopic images showing the expression of FLNa in A7 cells but not in M2 cells. The distributions of PrP and actin in M2 and A7 cells also differ greatly. For cytoplasmic staining with organelle specific markers, a FITC conjugated rabbit anti-calnexin antibody was used to mark the ER, and a BodipyTMF-05 ceramide BSA complex was used to locate Golgi. (D) Immunoblots show that in A7 cells PrP co-purifies with FLNa and vice versa. Loading controls show immunoblotting results of the respective cell lysates prior to immunoprecipitation with either anti-PrP or anti-FLNa mAb. (E) Immunoblots show that co-purification of FLNa with PrP can be competed with a synthetic peptide corresponding to the PrP-GPI-PSS sequence. Competition is peptide concentration dependent. An irrelevant synthetic peptide did not compete at the highest concentration tested. (F). Photographs of confocal microscopic images showing the co-localization of pro-PrP and FLNa in A7 cells. The difference in staining pattern seen between anti-PrP mAb and rabbit polyclonal anti-GPI-PSS antibody may reflect differences in the affinities of the antibodies, the availability of the epitope, or the second step antibody used for detecting the bound antibody. (G). Histograms show that cell surface PrP on A7 cells has a much longer halflife. Identical numbers of A7 and M2 cells were cultured in the presence brefel$^{din A}$ (BFA), for various lengths of time, to prevent the transit of newly synthesized PrP to the cell s$^{urface}$. At different times after culture, cells were prepared and stained with an anti-PrP mAb, and the levels of cell surface PrP then quantified by flow cytometry.

Immunofluorescent staining followed by confocal microscopic observation further confirms the presence of FLNa in A7 cells but not in M2 cells (FIG. 13C). In A7 cells, most of the FLNa is associated with the inner membrane leaflet, in the leading edges (FIG. 13C, see arrows). On the other hand, the spatial distributions of PrP differ noticeably between M2 and A7 cells. In M2 cells, most of the PrP is on the cell membrane, in cell-cell contact areas (FIG. 13C, solid arrows). By contrast, in A7 cells, PrP is concentrated in the membrane ruffle areas (FIG. 13C, solid arrows), as well as in the cytosol (FIG. 13C, dashed arrows). In the cytosol, two-color staining with organelle specific markers, such as fluorescent-label C5 ceramide for Golgi, or calnexin for endoplasmic reticulum, revealed that some PrP is associated with the Golgi, and the endoplasmic reticulum (FIG. 13C, solid arrows). The distributions of actin filaments also differ between A7 and M2 cells (FIG. 13C). In M2 cells, actin filaments are more uniformly distributed around the periphery of the cells (FIG. 13C solid arrow). In A7 cells, the actin filaments are better organized with readily identifiable stress fibers (FIG. 13C, solid arrows), and are more concentrated in the leading edges, where PrP and FLNa are also localized (FIG. 13C, dashed arrow).

The GPI-PSS of PrP has an FLNa binding motif. First, we confirmed that pro-PrP indeed interacts with FLNa in A7 cells. Immunoblotting of proteins co-purified with PrP using an FLNa specific mAb reveals the presence of FLNa (FIG. 13D, top panel). Conversely, immunoblotting of proteins co-purified with FLNa in A7 cells using an anti-PrP mAb detects PrP (FIG. 13D, bottom panel). Second, co-purification of PrP and FLNa is inhibited by a synthetic peptide corresponding to the GPI-PSS of PrP, but not by an irrelevant control synthetic peptide (FIG. 13E). Third, by immunofluorescent staining, PrP and FLNa co-localize in A7 cells, in the leading edges (FIG. 13F). Staining with the anti-PrP-GPI-PSS antibody also shows the co-localization of pro-PrP and FLNa (FIG. 13F, solid arrows identify areas of co-localization).

Since PrP is physically associated with FLNa in A7 cells, we speculated that PrP on A7 cells might be more stable, and thus have a longer half-life. We found that on M2 cells, PrP has a half-life of about 5 to 6 hrs. In contrast, on A7 cells, the half-life of PrP is longer, approximately 10 to 12 hrs (FIG. 13G). Therefore, anchoring of cell surface PrP to FLNa stabilizes PrP on the cell surface.

Identification of the Binding Motifs on FLNa and the PrP GPI-PSS

We reported earlier that a full-length FLNa1-24 dimer binds PrP GPI-PSS but not a FLNa1-23 monomer, which lacks the last Ig-like dimerization domain, domain 24. Subsequently, we found that the pro-PrP binding domain on FLNa is located between domains 10 and 24. Next, we prepared individual FLNa C-terminal domains with a GST tag, which allows the individual domain to dimerize. We then determine which domain binds pro-PrP. We found that pro-PrP binds domains, 10, 16, 17, 18, 20, 21 or 23 but not domains, 11, 19, 22 or 24 (FIG. 14A). Thus, similar to other FLNa binding partners, pro-PrP binds to the C-terminal region of the FLNa.

The GPI-PSS of PrP has 22 residues. To further characterize the FLNa binding motif on the GPI-PSS, we created recombinant pro-PrP proteins that were truncated at different positions at the C-terminus (FIG. 14B). We found that the last 5 amino acids of the GPI-PSS are used for FLNa binding; pro-PrP, which lacks the last 5 amino acids is unable to bind FLNa. Therefore, the GPI-PSS of PrP is long enough to transverse the membrane, allowing it to interact with FLNa in the inner membrane leaflet.

Figure 14C:
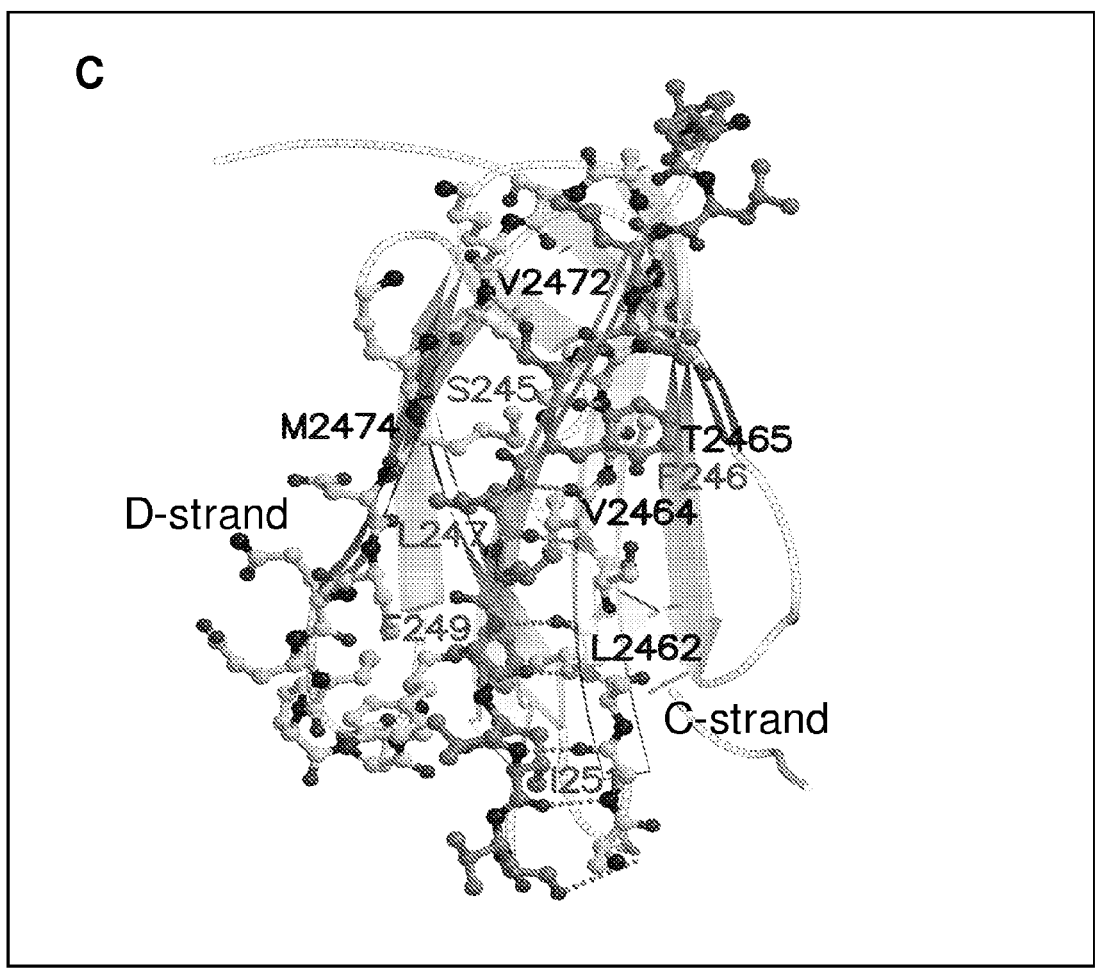
FIG. 14 illustrates the identification of the pro-PrP binding domains on FLNa and the residues in the GPI-PSS that are important in binding FLNa (A). FLNa contains multiple pro-PrP binding domains. Immunoblots of in vitro pull-down assays show that recombinant pro-PrP binds to domains 10, 15-16, 17, 18, 20, 21, and 23 but not domains 11, 19 22 or 24 of FLNa. (B) Immunoblots of in vitro pull-down assays show that the last 5 amino acids at the C-terminus of PrP GPI-PSS are important in FLNa binding. Pro-PrP lacking the last 5 amino acids is unable to bind FLNa. Furthermore, replacing two of the three polar residues in the last five amino acid of the GPI-PSS completely eliminated FLNa binding. (C). In silico model of a PrP GPI-PSS bound to domain 23 of FLNa.

The FLNa ligand-binding interface has multiple hydrophobic, non-polar amino acid contact residues. Based on this information, we predicted that amino acids at positions 246 (phenylalanine, F), 249 (F) or 250 (leucine, L) of the GPI-PSS might be critical for binding FLNa. Worthy of note is that these three residues are highly conserved in mammalian PrP (FIG. 14B). To test this hypothesis, we replaced these non-polar amino acids, either individually or in combinations, to polar amino acids, such as tryptophan (W) or tyrosine (Y). We found that replacing residue 246, 249 or 250 (FIG. 14C, lanes 4, 5, 6) individually to polar amino acid did not disrupt the binding of FLNa. However, replacing both 246 and 250 to polar amino acids complete eliminated the FLNa binding activity (lane 7). Therefore, non-polar residues at position 246 and 250 are important in FLNa binding.

An in silico model (FIG. 14D) shows that in addition to the non-polar amino acid residues, the binding of GPI-PSS of PrP in between C- and D-strands of FLNa domains is likely stabilized by hydrogen bonding, which occurs between side chain hydroxyl-group of Ser245 on the GPI-PSS and the main chain amino group of Val2472 on FLNa23. In addition, there are several favorable hydrophobic interactions between the binding partners. For example, Leu247, Phe249 and Ile251 of the GPI-PSS can pack in between the hydrophobic residues at the FLNa domains.

Interaction Between PrP and FLNa Modulates the Cytoskeleton and Regulates Cell Spreading and Migration in A7 Cells Next, we used multiple PrP specific shRNA sequences, which were either under the control of an inducible promoter or constitutively active to down regulate PrP expression in M2 and A7 cells. One of the inducible, PrP specific sequence, sh-RNA-10, inhibited the expression of PrP in M2 and A7 cells by about 80-90% (FIG. 15A). Another inducible PrP specific sequence, shRNA-3 (shRNA-C) inhibited PrP expression by less than 5% (FIG. 15A). Similarly, constitutively active, PrP specific, shRNA-10, and shRNA-12 inhibited the expression of PrP by about 50-70% in M2 and A7 cells (FIG. 15A). In subsequent experiments, cells with either inducible shRNA-3 (shRNA-C) or constitutively active "scrambled" shRNA (shRNA-S) were used as controls.

Reducing PrP expression in A7 cells did not change the expression level of FLNa (FIG. 15A). However, in these cells the spatial distribution of FLNa is markedly altered. In control cells, FLNa is either associated with the membrane (FIG. 15B, top left panel, solid arrow) or concentrated in the leading edges (FIG. 15B top right panel, solid arrows). In PrP down regulated A7 cells, the level of membrane associated FLNa is decreased (FIG. 15B, bottom left panel, solid arrow) or retracted from the inner membrane leaflet (FIG. 15B, bottom right panel, solid arrows). This staining pattern is similar to the pattern seen in PrP down regulated pancreatic cancer lines.

Since FLNa binds and organizes actin filament, we also determined whether down-regulation of PrP causes the reorganization of the actin filaments in A7 cells. In control A7 cells with shRNA-S, the actin filaments are well organized (FIG. 15B, top two panels, solid arrows). In PrP down regulated A7 cells, the actin filaments are less well organized, and tend to concentrate in certain areas of the cells (FIG. 15B, bottom two panels, solid arrows).

Cofilin regulates actin filament organization by controlling its polymerization and de-polymerization. Two kinases, LIMK1 and 2, phosphorylate and inactivate cofilin. Consistently with these views, we found that the levels of p-cofilin and p-LIMK-1 are greatly reduced in PrP down-regulated A7 cells (FIG. 15C). We were unable to detect LIMK2 in M2 and A7 cells (n.s.).

M2 cells are deficient in spreading and migration compared to A7 cells, this deficiency has been attributed to the absence of FLNa in M2 cells. Binding of pro-PrP to FLNa might be the underlying mechanism by which A7 cells spread and migrate more efficiently. First, we confirmed that our A7 cells indeed migrate much more readily than M2 cells in a wound-healing assay. Second, we demonstrated that down regulation of PrP in M2 and A7 cells did not change the proliferation of M2 and A7 cells, especially at 2 and 4 days after culture. However, at 6 days after culture, down regulation of PrP in both M2 and A7 cells did slightly reduce their proliferation.

Finally, we compared the spreading and migration of PrP down regulated A7 cells with control A7 cells. Reducing PrP expression greatly diminishes the spreading (FIGS. 15E & F, in E, solid arrows identify adherent cells, dashed arrows identify non-adherent cells), and migration of A7 cells (FIG. 15 G-I). As expected, M2 cells with reduced PrP expression remain deficient in spreading and motility (n.s.). Collectively, these results provide strong evidence that the enhanced-cell spreading and migration observed in A7 cells is not solely due to the presence of FLNa, but rather due to the interactions between FLNa and pro-PrP.

Pro-PrP Enhances the Binding of FLNa to Integrin β1, and Interplays Between Pro-PrP, FLNa and Integrin β1 Regulate Cell Spreading and Migration Integrins are bidirectional, allosteric signaling molecules that control cell spreading and migration. FLNa binds to the cytoplasmic tail of integrin β chain, and modulates cell adhesion and migration. We next investigated whether binding of pro-PrP interferes with the binding of FLNa to integrin β chain. We found that A7 cells have substantially more integrin β1 than M2 cells (FIG. 16A). On the other hand, talin, which is also a binding partner of integrin β1, is expressed in a comparable level in M2 and A7 cells.

Since FLNa binds pro-PrP as well as integrin β1, we investigated whether in A7 cells, FLNa, integrin β1 and PrP co-exist in a complex. By immunofluorescent staining, some PrP and integrin β1 are co-localized. By immunoprecipitation, FLNa also co-purified with PrP, and FLNa with integrin β1. However, we were unable to co-purify integrin β1 with PrP and vice versa (FIG. 16B). These results suggest that FLNa, integrin β1, and PrP do not co-exist in a stable, trimeric complex; they exist in two independent complexes, one contains FLNa and PrP, the other contains FLNa and integrin β1.

Figure 17A:
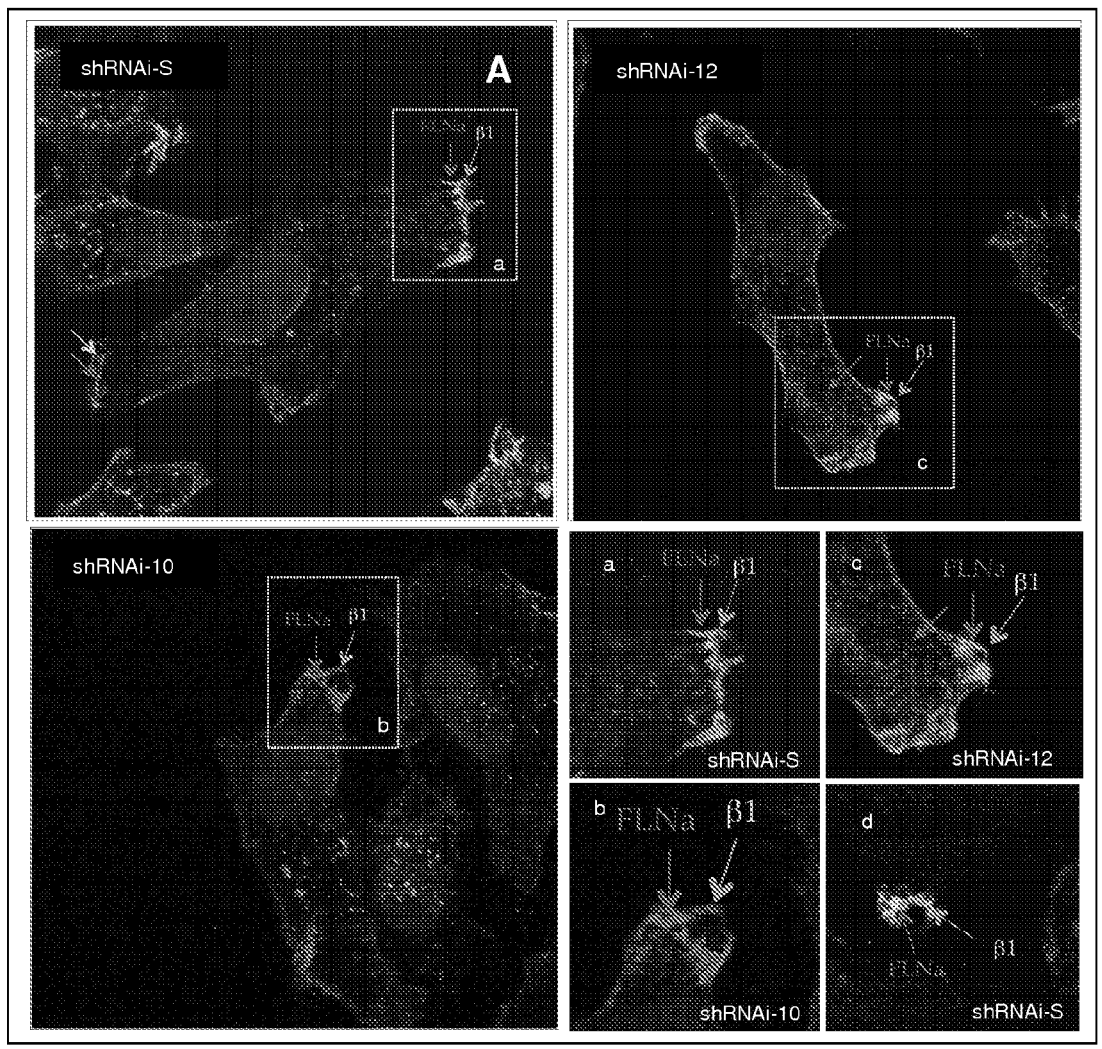
FIG. 17 illustrates down regulation of PrP alters the interaction between FLNa and integrin β1, and reduces the level of p-FAK. (A). Two color immunofluorescent staining and confocal microscopic images showing that co-localization of FLNa and integrin in A7-shRNA-S, control cells. In PrP down-regulated A7 cells, integrin β1 is separated from FLNa. The smaller images (a, b, c) were the areas of the larger images encircled in a dashed rectangular. Smaller images (d), was form the leading edge area of a different control, A7-shRNA-S, cell. (B). Down regulation of PrP in A7 cells reduces the level of p-FAK but not p-Src.

Next, we investigated whether expression of PrP influence the level of FLNa bound to integrin β1. First, we demonstrated that PrP down regulated A7 cells and control A7 cells have comparable levels of cell surface integrin β1 (FIG. 16C) as well as total integrin β1 (FIG. 16D). Next, we compared the amount of FLNa co-purified with integrin β1 in control A7 cells with the amount co-purified in PrP down-regulated A7 cells. We found that the amount of FLNa co-purified with integrin β1 is greatly reduced in PrP down-regulated A7 cells (FIG. 16E, compare lanes 5 to 6). Therefore, while down-regulation of PrP does not alter the expression of total integrin β1, it does reduce the amount of integrin β1 bound to FLNa. In PrP down-regulated A7 cells FLNa is retracted from the inner membrane leaflets (FIG. 16B). We suggest that this spatial change is the reason that less integrin β1 is bound to FLNa in PrP down regulated A7 cells; FLNa is disconnected form integrin β1. Two-color immunofluorescent staining results of integrin β1 and FLNa in PrP down regulated A7 cells support this view. In control cells, integrin β1 and FLNa are co-localized in the leading edges (FIG. 17A). In PrP down regulated A7 cells, FLNa is retracted from the cell surface, more FLNa is seen in the cytosol, and cell surface integrin β1 is not longer in close contact with FLNa (FIG. 17A).

Figure 17B:
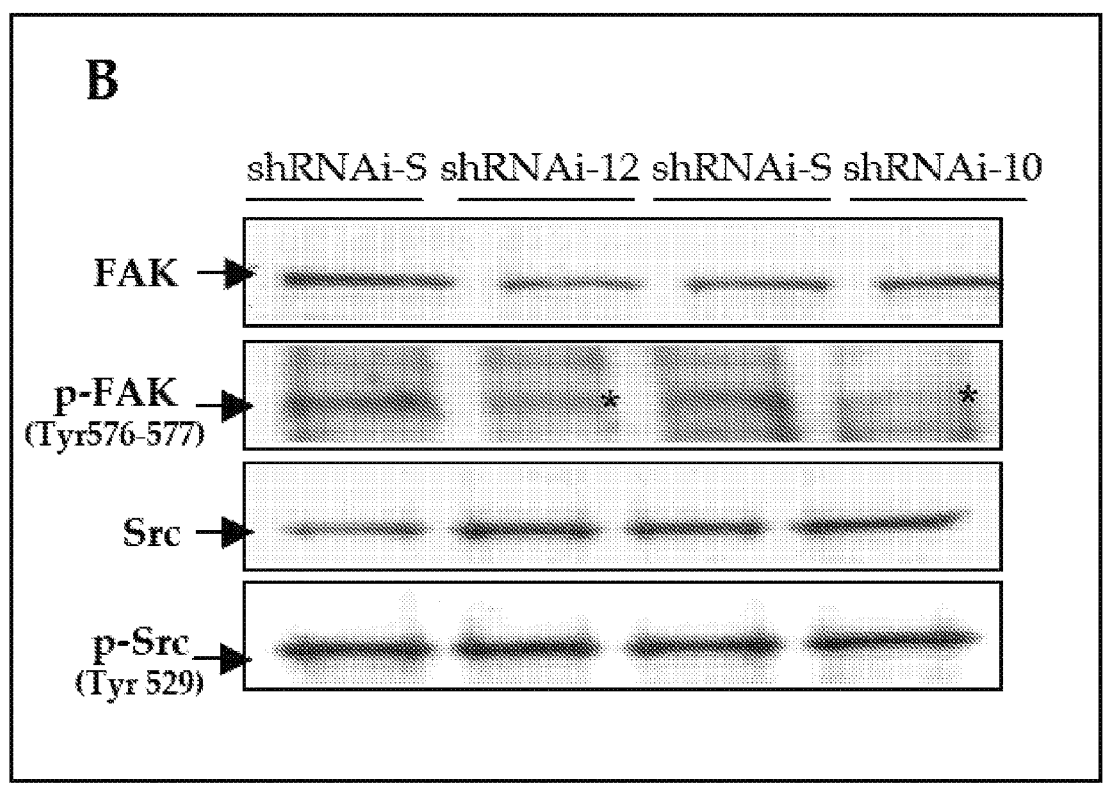

A major component of the integrin-signaling cascade is the focal adhesion kinase, FAK. Accordingly, the level of p-FAK is reduced in PrP down-regulated A7 cells (FIG. 17B). On the other hand, the level of p-Src, which is also important in integrin-signaling cascade, did not change.

A PrP GPI-PSS Synthetic Blocks Cell Spreading and Migration

We reported earlier that a peptapeptide, KKRPK (SEQ ID NO: 7), has cell penetrating capacity, in a $Ca^{++}$ dependent manner. More recently, we found that if the cells were incubated with the peptide for an extended period of time (>1 hr), the peptide can enter the cells without $Ca^{2+}$ (n.s.). We hypotheized that if we add a KKRPK (SEQ ID NO: 7) motif to the N-terminus of the PrP GPI-PSS, the KKRPK-GPI-PSS peptide may be able to enter cells, and compete for the binding of pro-PrP to FLNa.

The KKRPK-GPI-PSS (SEQ ID NO: 8) synthetic peptide is not toxic, and did not alter the cell surface expression of either PrP or integrin β1 (FIG. 18A), or the total levels of PrP, FLNa or integrin β1 in A7 cells (FIG. 18B). However, when A7 cells were first incubated with the synthetic peptide their spreading (FIG. 18C & D) and migration (FIG. 18E-G) were significantly reduced. We consistently achieved approximately 50-60% inhibition of cellular motility with 5 µM of the peptide; a significant inhibition is achieved with as little as 0.5 µM of the synthetic peptide. Control peptide, which also contains KKRPK (SEQ ID NO: 7) but with irrelevant amino acids, did not interfere with either cell spreading or motility at the highest concentration (5 µM) tested. Collectively, these experiments provide additional evidence that binding of pro-PrP to FLNa is important A7 cell spreading and migration, and this interaction can be partially inhibited with the PrP-GPI-PSS, which contains the FLNa binding motif.

Example 3

Figure 19:
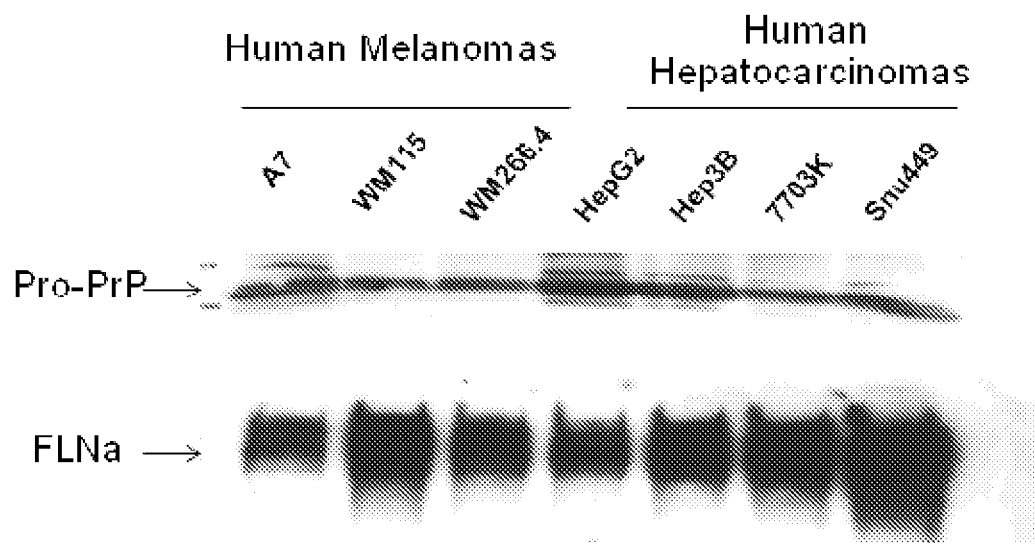
FIG. 19 illustrates the detection of PrP and FLNa expression in melanoma cell lines and in hepatocarcinoma cell lines: All studied cell lines express PrP as well as FLNa.

We investigated PrP expression in two additional human melanoma cell lines and four human hepatocarcinoma cell lines. When immunoblotted with anti-PrP mAb 8B4, A7 and two additional human melanoma cell lines, WM115 and WM 266.4, and four human hepatocarcinoma cell lines, HepG2, Hep3B, 7703K and Snu449 have a PrP species consistent with the molecular mass of pro-PrP (FIG. 19). All tumor cell lines also express FLNa.

Figure 20:
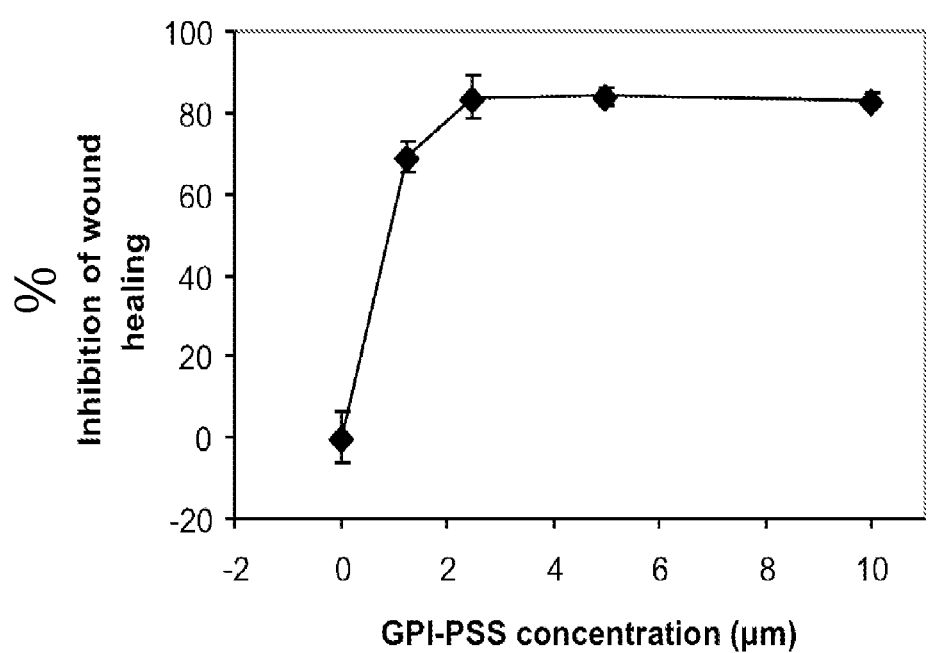
FIG. 20 illustrates the inhibition of hepatocarcinoma cell migration with the KKRPK-PrP-GPI-PSS (SEQ ID NO: 8) synthetic peptide: Various concentrations of the synthetic peptide were added at the beginning of the would-healing assay. At 16 hrs after the assay, the areas of the wound were imaged on a microscope equipped with a digital camera system and quantified Inhibition of cell migration was determined by comparing the healed area of non-treated cells with the healed area of cells treated either with the KKRPK-PrP-GPI-PSS peptide (SEQ ID NO: 8) or the KKRPK-control peptide (SEQ ID NO: 9).

We also the determined the effective of a KKRPK-PrP-GPI-PSS synthetic peptide (SEQ ID NO: 8) in inhibiting hepatocarcinoma cell migration in a wound-healing assay as described in example 2. As shown in FIG. 20, various concentrations of the synthetic peptide were added at the beginning of the would-healing assay. At 16 hrs after the assay, the areas of the wound were imaged on a microscope equipped with a digital camera system and quantified. Inhibition of cell migration was determined by comparing the healed area of non-treated cells with the healed area of cells treated either with the KKRPK-PrP-GPI-PSS peptide (SEQ ID NO: 8) or the KKRPK-control peptide (SEQ ID NO: 9). In vitro migration of one of the hepatocarcinoma cell line, HepG2, was inhibited with the KKRPK-GPI-PSS synthetic peptide (SEQ ID NO: 8).

Figure 21:
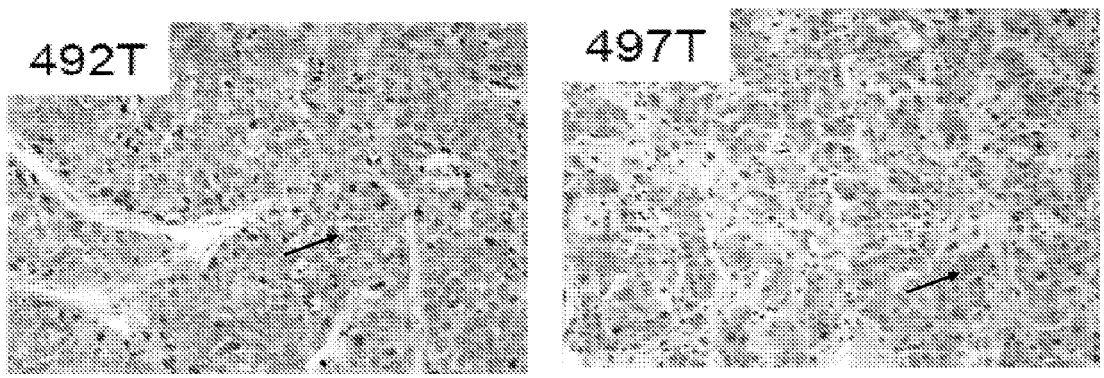
FIG. 21 illustrates the immunostaining of two cases of human hepatocarcinoma biopsies one 492T with high level of PrP immunoreactivity and the other 497T with moderate level of immunoreactivity (×40).

Finally, when immunostained with anti-PrP mAb 8H4, we found that three out of seven human hepatocarcinoma react (43%) with the anti-PrP mAb. Two of the positive hepatocarcinomas are shown in FIG. 21.

Collectively, these results provide strong evidence that similar to human pancreatic cancer, human melanomas and hepatocarcinomas also express pro-PrP. Expression of pro-PrP may also provide a growth advantage to these human cancers and detection of PrP expression may have prognostic or diagnostic value in these human cancers.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method of inhibiting adhesion, motility, migration, dispersal, and/or metastasis of a neoplastic, cancer, and/or tumorgenic cell in a subject, the cell expressing pro-prion protein (pro-PrP) and filamin A (FLNa), the method comprising:
administering to the cell a therapeutically effective amount of a pro-PrP regulating agent, the pro-PrP regulating agent comprising a peptide that inhibits binding of pro-PrP and FLNa in the cell, the peptide consisting of 5 to 16 amino acids and including an amino acid sequence selected from the group consisting of SEQ ID NO: 4, SEQ ID NO: 5, and SEQ ID NO: 6.

2. The method of claim 1, the peptide consisting of an amino acid sequence selected from the group consisting of SEQ ID NO: 2, SEQ ID NO: 3, SEQ ID NO: 4, SEQ ID NO: 5, and SEQ ID NO: 6.

3. The method of claim 1, the cancer cells comprising at least one of pancreatic adenocarcinoma cancer cell lines (PDAC), hepatocarcinoma cell lines, melanoma cell lines, colon carcinoma cell lines, gastric cancer cell lines, or colorectal cancer cell lines.

4. A method of treating a cancer in a subject, the cancer including cancer cells that express pro-PrP and FLNa, comprising:
administering to the cancer cells a therapeutically effective amount of a pro-PrP regulating agent, the pro-PrP regulating agent comprising a peptide that inhibits binding of pro-PrP and FLNa in the cell, the peptide consisting of 5 to 16 amino acids and including an amino acid sequence selected from the group consisting of SEQ ID NO: 4, SEQ ID NO: 5, and SEQ ID NO: 6.

5. The method of claim 4, the pro-PrP regulating agent being administered at an amount effective to inhibit cancer cell adhesion, motility, migration, dispersal, and/or metastasis.

6. The method of claim 4, the peptide consisting of an amino acid sequence selected from the group consisting of SEQ ID NO: 2, SEQ ID NO: 3, SEQ ID NO: 4, SEQ ID NO: 5, and SEQ ID NO: 6.

7. The method of claim 4, the cancer cells comprising at least one of pancreatic adenocarcinoma cancer cell lines (PDAC), hepatocarcinoma cell lines, melanoma cell lines, colon carcinoma cell lines, gastric cancer cell lines, or colorectal cancer cell lines.

8. The method of claim 1, the pro-PrP regulating agent further comprising a transport moiety to facilitate transport of the peptide within the cell.

9. The method of claim 8, the transport moiety comprising a peptide having an amino acid sequence of SEQ ID NO: 7.

10. The method of claim 1, the pro-PrP regulating agent having the amino acid sequence of SEQ ID NO: 8.

11. The method of claim 4, the pro-PrP regulating agent further comprising a transport moiety to facilitate transport of the peptide within the cancer cell.

12. The method of claim 11, the transport moiety comprising a peptide having an amino acid sequence of SEQ ID NO: 7.

13. The method of claim 4, the pro-PrP regulating agent having the amino acid sequence of SEQ ID NO: 8.

* * * * *

UNITED STATES PATENT AND TRADEMARK OFFICE
CERTIFICATE OF CORRECTION

PATENT NO. : 9,492,472 B2  
APPLICATION NO. : 13/141437  
DATED : November 15, 2016  
INVENTOR(S) : Man Sun Sy et al.

Page 1 of 1

It is certified that error appears in the above-identified patent and that said Letters Patent is hereby corrected as shown below:

In the Specification

Column 1, after Line 11 insert:
--GOVERNMENT FUNDING
This invention was made with government support under Grant No. CA133559 awarded by The National Institute of Health. The United States government has certain rights in the invention.--

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 18

<210> SEQ ID NO 1
<211> LENGTH: 24
<212> TYPE: PRT
<213> ORGANISM: Homo sapiens

<400> SEQUENCE: 1

Gly Ser Ser Met Val Leu Phe Ser Ser Pro Val Ile Leu Leu Ile
1               5                   10                  15

Ser Phe Ile Phe Leu Ile Val Gly
            20

<210> SEQ ID NO 2
<211> LENGTH: 16
<212> TYPE: PRT
<213> ORGANISM: Homo sapiens

<400> SEQUENCE: 2

Pro Pro Val Ile Leu Leu Ile Ser Phe Leu Ile Phe Leu Ile Val Gly
1               5                   10                  15

<210> SEQ ID NO 3
<211> LENGTH: 8
<212> TYPE: PRT
<213> ORGANISM: Homo sapiens
```

```
<400> SEQUENCE: 3

Phe Leu Ile Phe Leu Ile Val Gly
1               5

<210> SEQ ID NO 4
<211> LENGTH: 5
<212> TYPE: PRT
<213> ORGANISM: Homo sapiens

<400> SEQUENCE: 4

Phe Leu Ile Val Gly
1               5

<210> SEQ ID NO 5
<211> LENGTH: 8
<212> TYPE: PRT
<213> ORGANISM: Homo sapiens
<220> FEATURE:
<221> NAME/KEY: Xaa
<222> LOCATION: (1)..(1)
<223> OTHER INFORMATION: Xaa is a neutral non-polar amino acid
<220> FEATURE:
<221> NAME/KEY: Xaa
<222> LOCATION: (4)..(4)
<223> OTHER INFORMATION: Xaa is a neutral non-polar amino acid
<220> FEATURE:
<221> NAME/KEY: Xaa
<222> LOCATION: (5)..(5)
<223> OTHER INFORMATION: Xaa is a neutral non-polar amino acid

<400> SEQUENCE: 5

Xaa Leu Ile Xaa Xaa Ile Val Gly
1               5

<210> SEQ ID NO 6
<211> LENGTH: 14
<212> TYPE: PRT
<213> ORGANISM: Homo sapiens
<220> FEATURE:
<221> NAME/KEY: Xaa
<222> LOCATION: (7)..(7)
<223> OTHER INFORMATION: Xaa is a neutral non-polar amino acid
<220> FEATURE:
<221> NAME/KEY: Xaa
<222> LOCATION: (10)..(10)
<223> OTHER INFORMATION: Xaa is a neutral non-polar amino acid
<220> FEATURE:
<221> NAME/KEY: Xaa
<222> LOCATION: (11)..(11)
<223> OTHER INFORMATION: Xaa is a neutral non-polar amino acid

<400> SEQUENCE: 6

Val Ile Leu Leu Ile Ser Xaa Leu Ile Xaa Xaa Ile Val Gly
1               5                   10

<210> SEQ ID NO 7
<211> LENGTH: 5
<212> TYPE: PRT
<213> ORGANISM: Homo sapiens

<400> SEQUENCE: 7

Lys Lys Arg Pro Lys
1               5

<210> SEQ ID NO 8
<211> LENGTH: 21
<212> TYPE: PRT
<213> ORGANISM: Homo sapiens
```

```
<400> SEQUENCE: 8

Lys Lys Arg Pro Lys Pro Pro Val Ile Leu Leu Ile Ser Phe Leu Ile
1               5                   10                  15

Phe Leu Ile Val Gly
            20

<210> SEQ ID NO 9
<211> LENGTH: 26
<212> TYPE: PRT
<213> ORGANISM: Homo sapiens

<400> SEQUENCE: 9

Lys Lys Arg Pro Lys Asp Met Asp Tyr Leu Pro Arg Val Pro Asn Gln
1               5                   10                  15

Gly Ile Ile Ile Asn Pro Met Leu Ser Asp
            20                  25

<210> SEQ ID NO 10
<211> LENGTH: 9
<212> TYPE: PRT
<213> ORGANISM: Homo sapiens

<400> SEQUENCE: 10

Phe Arg Ser Ser Leu Phe Leu Trp Val
1               5

<210> SEQ ID NO 11
<211> LENGTH: 9
<212> TYPE: PRT
<213> ORGANISM: Homo sapiens

<400> SEQUENCE: 11

Tyr Lys Ser Ala Val Thr Thr Val Val
1               5

<210> SEQ ID NO 12
<211> LENGTH: 9
<212> TYPE: PRT
<213> ORGANISM: Homo sapiens

<400> SEQUENCE: 12

Phe Lys Glu Ala Thr Thr Thr Val Met
1               5

<210> SEQ ID NO 13
<211> LENGTH: 9
<212> TYPE: PRT
<213> ORGANISM: Homo sapiens

<400> SEQUENCE: 13

Tyr Lys Glu Ala Thr Ser Thr Phe Thr
1               5

<210> SEQ ID NO 14
<211> LENGTH: 9
<212> TYPE: PRT
<213> ORGANISM: Homo sapiens

<400> SEQUENCE: 14

Tyr Lys Ser Ala Ile Thr Thr Thr Ile
1               5
```

```
<210> SEQ ID NO 15
<211> LENGTH: 9
<212> TYPE: PRT
<213> ORGANISM: Homo sapiens

<400> SEQUENCE: 15

Thr Arg Thr Ser Leu Lys Tyr Met Ser
1               5

<210> SEQ ID NO 16
<211> LENGTH: 9
<212> TYPE: PRT
<213> ORGANISM: Homo sapiens

<400> SEQUENCE: 16

Leu Ser Thr Ser Leu Lys Leu Gly Pro
1               5

<210> SEQ ID NO 17
<211> LENGTH: 9
<212> TYPE: PRT
<213> ORGANISM: Homo sapiens

<400> SEQUENCE: 17

Phe Ser Thr Phe Gly Glu Leu Thr Val
1               5

<210> SEQ ID NO 18
<211> LENGTH: 14
<212> TYPE: PRT
<213> ORGANISM: Homo sapiens

<400> SEQUENCE: 18

Val Ile Leu Leu Ile Ser Phe Leu Ile Phe Leu Ile Val Gly
1               5                   10
```